United States Patent
Eldridge et al.

(10) Patent No.: US 9,149,522 B2
(45) Date of Patent: *Oct. 6, 2015

(54) COMPOSITIONS OF VACCINES AND ADJUVANTS AND METHODS FOR THE TREATMENT OF URINARY TRACT INFECTIONS

(71) Applicant: Sequoia Sciences, Inc, St. Louis, MO (US)

(72) Inventors: Gary Eldridge, St. Louis, MO (US); Steven M Martin, St. Louis, MO (US)

(73) Assignee: Sequoia Sciences, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/663,690

(22) Filed: Mar. 20, 2015

(65) Prior Publication Data

US 2015/0216969 A1    Aug. 6, 2015

Related U.S. Application Data

(63) Continuation-in-part of application No. 14/494,001, filed on Sep. 23, 2014, now Pat. No. 9,017,698.

(60) Provisional application No. 61/882,498, filed on Sep. 25, 2013.

(51) Int. Cl.
| | |
|---|---|
| A61K 47/02 | (2006.01) |
| A61K 39/39 | (2006.01) |
| A61K 39/108 | (2006.01) |
| A61K 39/00 | (2006.01) |

(52) U.S. Cl.
CPC .............. *A61K 39/39* (2013.01); *A61K 39/0258* (2013.01); *A61K 2039/545* (2013.01); *A61K 2039/55511* (2013.01); *A61K 2039/55572* (2013.01)

(58) Field of Classification Search
None
See application file for complete search history.

(56) References Cited

U.S. PATENT DOCUMENTS

| | | |
|---|---|---|
| 6,500,434 B1 | 12/2002 | Langermann et al. |
| 6,737,063 B2 | 5/2004 | Langermann et al. |
| 6,913,750 B2 | 7/2005 | Hultgren et al. |
| 8,231,881 B2 | 7/2012 | Bhatia et al. |
| 8,273,361 B2 | 9/2012 | Reed et al. |
| 8,343,512 B2 | 1/2013 | Reed et al. |
| 8,410,258 B2 | 4/2013 | Goto et al. |
| 8,425,919 B2 | 4/2013 | Goto et al. |
| 8,486,414 B2 | 7/2013 | Reed et al. |
| 8,609,114 B2 | 12/2013 | Reed |
| 8,722,064 B2 | 5/2014 | Reed et al. |
| 8,771,710 B2 | 7/2014 | Bhatia et al. |
| 8,840,908 B2 | 9/2014 | Reed et al. |
| 2002/0086037 A1 | 7/2002 | Hultgren et al. |
| 2003/0099665 A1 | 5/2003 | Hultgren et al. |
| 2003/0138449 A1 | 7/2003 | Langermann et al. |
| 2003/0199071 A1 | 10/2003 | Hultgren et al. |
| 2008/0131466 A1 | 6/2008 | Reed et al. |
| 2009/0041798 A1 | 2/2009 | Reed et al. |
| 2009/0291099 A1 | 11/2009 | Goto et al. |
| 2010/0129391 A1 | 5/2010 | Reed et al. |
| 2010/0310602 A1 | 12/2010 | Reed et al. |
| 2011/0105383 A1 | 5/2011 | Hook et al. |
| 2011/0200640 A1 | 8/2011 | Hotez et al. |
| 2011/0305748 A1 | 12/2011 | Clegg et al. |
| 2012/0082700 A1 | 4/2012 | Dickey et al. |
| 2012/0114688 A1 | 5/2012 | Bhatia et al. |
| 2012/0177683 A1 | 7/2012 | Anderson et al. |
| 2012/0263754 A1 | 10/2012 | Dubensky, Jr. et al. |
| 2012/0328655 A1 | 12/2012 | Dubensky, Jr. et al. |
| 2013/0108692 A1 | 5/2013 | Anderson et al. |
| 2013/0177584 A1 | 7/2013 | Goto et al. |
| 2013/0177625 A1 | 7/2013 | Kim et al. |
| 2013/0195910 A1 | 8/2013 | Harn et al. |
| 2013/0209500 A1 | 8/2013 | Reed et al. |
| 2013/0236492 A1 | 9/2013 | Baudner et al. |
| 2013/0266612 A1 | 10/2013 | Fukasaka et al. |
| 2013/0273094 A1 | 10/2013 | McLeod et al. |
| 2013/0273149 A1 | 10/2013 | Shaw et al. |
| 2013/0309273 A1 | 11/2013 | Hassett et al. |

(Continued)

FOREIGN PATENT DOCUMENTS

| | | |
|---|---|---|
| WO | WO 00/50073 A2 | 8/2000 |
| WO | WO 01/04148 A2 | 1/2001 |

(Continued)

OTHER PUBLICATIONS

Misquith, et al. In vitro evaluation of TLR4 agonist activity: Formulation effects. Colloids Surf B Biointerfaces, Sep. 19, 2013.

International Search Report and Written Opinion of the International Searching Authority for PCT/IB1464813; date of mailing Apr. 16, 2015.

Bertholet et al. A defined tuberculosis vaccine candidate boosts BCG and protects against multidrug-resistant Mycobacterium tuberculosis. Sci Transl Med. 2010, 2(53), 53ra74.

Baldwin et al. Enhanced humoral and Type 1 cellular immune responses with Fluzone adjuvanted with a synthetic TLR4 agonist formulated in an emulsion. Vaccine, 2009, 27, p. 5956-5963.

Cong et al. Human immunome, bioinformatic analyses using HLA supermotifs and the parasite genome, binding assays, studies of human T cell responses, and immunization of HLA-A 1101 transgenic mice including novel adjuvants provide a foundation for HLA-A03 restricted CD8+T cell epitope based, adjuvanted vaccine protective against Toxoplasma gondii. Immunome Research, 2010, 6:12.

(Continued)

*Primary Examiner* — Brian J Gangle
(74) *Attorney, Agent, or Firm* — Christopher Casieri

(57) ABSTRACT

This invention describes novel adjuvant compositions and formulations with excellent stability at refrigerated and room temperatures and up to and about 37° C. that can be produced at remarkably low costs. This invention describes novel vaccine compositions and formulations to treat and prevent urinary tract infections caused by gram-negative bacteria including *Escherichia coli* and multi-drug resistant *E. coli*. This invention also describes methods of administration of said novel vaccine compositions and formulations and methods of treatment to prevent and treat urinary tract infections caused by gram-negative bacteria including *E. coli* and multi-drug resistant *E. coli*.

30 Claims, 4 Drawing Sheets

(56) References Cited

U.S. PATENT DOCUMENTS

| | | |
|---|---|---|
| 2013/0323280 A1 | 12/2013 | Anderson et al. |
| 2014/0023674 A1 | 1/2014 | Tuomanen et al. |
| 2014/0079709 A1 | 3/2014 | Aman et al. |
| 2014/0099337 A1 | 4/2014 | Davis et al. |
| 2014/0127247 A1 | 5/2014 | Dubensky, Jr. et al. |
| 2014/0147458 A1 | 5/2014 | Kim et al. |
| 2014/0155277 A1 | 6/2014 | Wiley |
| 2014/0227309 A1 | 8/2014 | Smith et al. |
| 2014/0308291 A1 | 10/2014 | Aman et al. |

FOREIGN PATENT DOCUMENTS

| | | |
|---|---|---|
| WO | WO 01/05978 A1 | 1/2001 |
| WO | WO 2008/153541 A1 | 12/2008 |
| WO | WO 2009/143457 A2 | 11/2009 |
| WO | WO 2009/155489 A2 | 12/2009 |
| WO | WO 2010/141861 A1 | 12/2010 |
| WO | WO 2011/002522 A2 | 1/2011 |
| WO | WO 2011/005769 A1 | 1/2011 |
| WO | WO 2011/005772 A1 | 1/2011 |
| WO | WO 2011/112871 A1 | 9/2011 |
| WO | WO 2012/006367 A2 | 1/2012 |
| WO | WO 2012/097347 A1 | 7/2012 |
| WO | WO 2012/134975 A1 | 10/2012 |
| WO | WO 2012/141984 A1 | 10/2012 |
| WO | WO 2012/149307 A2 | 11/2012 |
| WO | WO 2012/158978 A1 | 11/2012 |
| WO | WO 2013/072768 A2 | 5/2013 |
| WO | WO 2013/119954 A1 | 8/2013 |
| WO | WO 2013/155448 A1 | 10/2013 |
| WO | WO 2014/168821 A1 | 10/2014 |
| WO | WO 2014/172637 A1 | 10/2014 |

OTHER PUBLICATIONS

Bertholet et al. Optimized subunit vaccine protects against experimental leishmaniasis. Vaccine, 2009, 27, p. 7036-7045.

Langermann et al. Prevention of mucosal Escherichia coli infection by FimH-adhesin-based systemic vaccination. Science, 1997, 276, p. 607-611.

Langermann et al. Vaccination with FimH adhesin protects cynomolgus monkeys from colonization and infection by uropathogenic Escherichia coli. J. Infectious Dis. 2000, 181, p. 774-8.

Langermann et al. Vaccination utilizing the FimCH complex as a strategy to prevent Escherichia coli urinary tract infections. J. Infectious Dis. 2001, 183(Suppl 1), p. S84-6.

Baldwin et al. The ID93 Tuberculosis Vaccine Candidate Does Not Induce Sensitivity to Purified Protein Derivative. Clin. Vaccine Immunol., 2014, 21 (9), p. 1309-1313.

Duthie et al. Protection against Mycobacterium leprae Infection by the ID83/GLA-SE and ID93/GLA-SE Vaccines Developed for Tuberculosis. Infect. Immun., 2014, 82 (9), p. 3979-85.

Fox et al. A Nanoliposome Delivery System to Synergistically Trigger TLR4 and TLR7. J. Nanobiotechnology. 2014, 12(17), p. 1-9.

Zhang et al. Longevity of Sm-p80-specific antibody responses following vaccination with Sm-p80 vaccine in mice and baboons and transplacental transfer of Sm-p80-specific antibodies in a baboon. Parasitol Res. 2014, 113(6), p. 2239-50.

Clegg et al. GLA-AF, an emulsion-free vaccine adjuvant for pandemic influenza. PloS One. 2014, 9(2). e88979.

McKay et al. Glucopyranosyl lipid A adjuvant significantly enhances HIV specific T and B cell responses elicited by a DNA-MVA-protein vaccine regimen. PloS One. 2014, 9(1), e84707.

Orr et al. A dual TLR agonist adjuvant enhances the immunogenicity and protective efficacy of the tuberculosis vaccine antigen ID93. PloS One. 2014, 9(1), e83884.

Orr et al. Elimination of the cold-chain dependence of a nanoemulsion adjuvanted vaccine against tuberculosis by lyophilization. J. Controlled Release. 2014, 177, p. 20-26.

Fox et al. Cryogenic transmission electron microscopy of recombinant tuberculosis vaccine antigen with anionic liposomes reveals formation of flattened liposomes. Int. J. Nanomedicine. 2014, 9, p. 1367-1377.

Karmakar et al. Cross-species protection: Schistosoma mansoni Sm-p80 vaccine confers protection against Schistosoma haematobium in hamsters and baboons. Vaccine. 2014, 32, p. 1296-1303.

Shanley et al. Therapeutic vaccination against relevant high virulence clinical isolates of Mycobacterium tuberculosis. Tuberculosis. 2014, 94, p. 140-147.

Gupta et al. Production and preclinical evaluation of Plasmodium falciparum MSP-119 and MSP-311 chimeric protein, PfMSP-Fu24. Clin. Vaccine Immunol. 2014, 21(6), p. 886-897.

Nkolola et al. Comparison of multiple adjuvants on the stability and immunogenicity of a clade C HIV-1 gp140 trimer. Vaccine, 2014, 32, p. 2109-2116.

Dowling et al. Modulating potency: physicochemical characteristics are a determining factor of TLR4-agonist nanosuspension activity. J. Pharmaceutical Sciences, 2014, 103, p. 879-889.

Singh et al. Immunogenic potential of latency associated antigens against Mycobacterium tuberculosis. Vaccine, 2014, 32, p. 712-716.

Fox et al. TLR4 ligand formulation causes distinct effects on antigen-specific cell-mediated and humoral immune responses. Vaccine, 2013, 31, 5848-5855.

Jones et al. Immunisation with ID83 fusion protein induces antigen-specific cell mediated and humoral immune responses in cattle. Vaccine, 2013, 31, p. 5250-5255.

Orr et al. Adjuvant formulation structure and composition are critical for the development of an effective vaccine against tuberculosis. J. Controlled Release, 2013, 172, p. 190-200.

Baldwin et al. Protection against tuberculosis with homologous or heterologous protein/vector vaccine approaches is not dependent on CD8+ T cells. J. Immunol. 2013, 191(5), p. 2514-2525.

Orr et al. Cooperative intracellular interactions between MyD88 and TRIF are required for CD4 T cell TH1 polarization with a synthetic TLR4 agonist adjuvant. Eur J. Immunol, 2013, 43(9), doi:10.1002/eji.201243124.

Li et al. HIV/SIV DNA vaccine combined with protein in a co-immunization protocol elicits highest humoral responses to envelope in mice and macaques. Vaccine, 2013, 31, p. 3747-3755.

Duthie et al. Development and pre-clinical assessment of a 73 kD chimeric fusion protein as a defined sub-unit vaccine for leprosy. Vaccine, 2013, 31, p. 813-819.

Treanor et al. Evaluation of safety and immunogenicity of recombinant influenza hemagglutinin (H5/ Indonesia/May 2005) formulated with and without a stable oil-in-water emulsion containing glucopyranosyl-lipid A (SE +GLA) adjuvant. Vaccine, 2013, 31(48), p. 5760-5.

Cespedes et al. Antigenicity and immunogenicity of a novel chimeric peptide antigen based on the P. vivax circumsporozoite protein. Vaccine, 2013, 31, p. 4923-4930.

Fox et al. Technology transfer of oil-in-water emulsion adjuvant manufacturing for pandemic influenza vaccine production in Romania. Vaccine, 2013, 31, p. 1633-1640.

Coler et al. Therapeutic Immunization against Mycobacterium tuberculosis Is an Effective Adjunct to Antibiotic Treatment. J. Infectious Dis. 2013, 207, p. 1242-1252.

Kastenmuller et al. Full-Length Plasmodium falciparum Circumsporozoite Protein Administered with Long-Chain Poly(I•C) or the Toll-Like Receptor 4 Agonist Glucopyranosyl Lipid Adjuvant-Stable Emulsion Elicits Potent Antibody and CD4+ T Cell Immunity and Protection in Mice. Infect. Immunity. 2013, 81(3), p. 789-800.

Fung et al. Optimizing manufacturing and composition of a TLR4 nanosuspension: physicochemical stability and vaccine adjuvant activity. J. Nanobiotechnology, 2013, 11:43, doi:10.1186/1477-3155-11-43.

Clegg et al. Adjuvant solution for pandemic influenza vaccine production. PNAS, 2012, 109(43), p. 17585-17590.

Fox et al. Effects on immunogenicity by formulations of emulsion-based adjuvants for malaria vaccines. Clin. Vaccine Immunol. 2012, 19(10), p. 1633-1640.

Arias et al. Glucopyranosyl Lipid Adjuvant (GLA), a Synthetic TLR4 agonist, promotes potent systemic and mucosal responses to intranasal immunization with HIVgp140. PloS ONE, 2012, 7(7), e41144.

(56) References Cited

OTHER PUBLICATIONS

Schneider, et al. Intradermally administered TLR4 agonist GLA-SE enhances the capacity of human skin DCs to activate T cells and promotes emigration of Langerhans cells. Vaccine, 2012, 30, p. 4216-4224.

Gomes et al. KSAC, a defined Leishmania antigen, plus adjuvant protects against the virulence of L. major transmitted by its natural vector Phlebotomus duboscqi. PloS ONE, 2012, 6(4), e1610.

Lumsden et al. Evaluation of immune responses to a Plasmodium vivax CSP-based recombinant protein vaccine candidate in combination with second-generation adjuvants in mice. Vaccine, 2012, 30, p. 3311-3319.

Xiao et al. A TLR4 agonist synergizes with dendritic cell-directed lentiviral vectors for inducing antigen-specific immune responses. Vaccine, 2012, 30 (15), p. 2570-2581.

Baldwin et al. The importance of adjuvant formulation in the development of a tuberculosis vaccine. J. Immunol. 2012, 188(5), p. 2189-2197.

Behzad et al. GLA-SE, a synthetic toll-like receptor 4 agonist, enhances T-cell responses to influenza vaccine in older adults. J. Infectious Dis. 2012, 205 (3), p. 466-473.

Lambert et al. Molecular and cellular response profiles induced by the TLR4 agonist-based adjuvant Glucopyranosyl Lipid A. PloS ONE, 2012, 7(12), e51618.

Peters et al. Evaluation of recombinant Leishmania polyprotein plus glucopyranosyl lipid a stable emulsion vaccines against sand fly-transmitted Leishmania major in C57BL/6 mice. J. Immunol. 2012, 189, p. 4832-4841.

Adhikari et al. Novel structurally designed vaccine for S. aureus α-hemolysin: protection against bacteremia and pneumonia. PloS ONE, 2012, 7(6), e38567.

Daifalla et al. Leishmania donovani recombinant iron superoxide dismutase B1 protein in the presence of TLR-based adjuvants induces partial protection of BALB/c mice against Leishmania major infection. Experimental Parasitology, 2012, 131, p. 317-324.

Cong et al. Toxoplasma gondii HLA-B*0702-restricted GRA7(20-28) peptide with adjuvants and a universal helper T cell epitope elicits CD8(+) T cells producing interferon-γ and reduces parasite burden in HLA-B*0702 mice. Hum Immunol. 2012, 73(1), p. 1-10.

Pantel et al. A new synthetic TLR4 agonist, GLA, allows dendritic cells targeted with antigen to elicit Th1 T-cell immunity in vivo. Eur J Immunol. 2012, 42(1), p. 101-109.

Windish et al. Protection of mice from Mycobacterium tuberculosis by ID87/GLA-SE, a novel tuberculosis subunit vaccine candidate. Vaccine, 2011, 29(44), p. 7842-7848.

Lumsden et al. Evaluation of the safety and immunogenicity in rhesus monkeys of a recombinant malaria vaccine for Plasmodium vivax with a synthetic Toll-like receptor 4 agonist formulated in an emulsion. Infect. Immunity, 2011, 79 (9), p. 3492-3500.

Lousada-Dietrich et al. A synthetic TLR4 agonist formulated in an emulsion enhances humoral and Type 1 cellular immune responses against GMZ2—a GLURP-MSP3 fusion protein malaria vaccine candidate. Vaccine, 2011, 29, p. 3284-3292.

Coler et al. Development and characterization of synthetic glucopyranosyl lipid adjuvant system as a vaccine adjuvant. PloS ONE, 2011, 6(1), e16333.

Cong et al. Towards an immunosense vaccine to prevent toxoplasmosis: protective Toxoplasma gondii epitopes restricted by HLA-A*0201. Vaccine, 2011, 29(4), p. 754-762.

Coler et al. A synthetic adjuvant to enhance and expand immune responses to influenza vaccines. PloS ONE, 2010, 5(10), e13677.

Anderson et al. Physicochemical characterization and biological activity of synthetic TLR4 agonist formulations. Colloids Surfaces B: Biomolecules, 2010, 75, p. 123-132.

COMPOSITIONS OF VACCINES AND ADJUVANTS AND METHODS FOR THE TREATMENT OF URINARY TRACT INFECTIONS

CROSS REFERENCE TO RELATED APPLICATIONS

This application is a continuation in part of U.S. application Ser. No. 14/494,001, which claims benefit of U.S. Provisional Application No. 61/882,498 filed on Sep. 25, 2013, the contents of which are incorporated in its entirety by reference.

The Sequence Listing in the ASCII text file named Sequence_ST25.txt created on May 27, 2015, which is 4.53 KB, is incorporated herein by reference.

BACKGROUND OF THE INVENTION

1. Field of the Invention

The invention provides novel adjuvant compositions and formulations with excellent stability at refrigerated and room temperatures, and also up to about 37° C., that can be produced at remarkably low costs. These novel adjuvant compositions and formulations are used in vaccines and exhibit superior properties of enhancing immune responses to antigens while causing less severe injection site and systemic reactions. The invention also describes novel vaccine compositions and formulations to treat and prevent urinary tract infections caused by gram-negative bacteria including *Escherichia coli* and multi-drug resistant *E. coli*. The invention also provides methods of administration of said novel vaccine formulations and methods of treatment to prevent and treat urinary tract infections caused by gram-negative bacteria including *E. coli* and multi-drug resistant *E. coli*.

2. Description of the Related Art

In the United States (US) and other countries most populations are protected from numerous infectious diseases by the use of vaccines. Vaccines protect people from infectious diseases such as diphtheria, tetanus, pertussis, hepatitis, influenza, and polio to name a few. Society relies on the protections afforded by vaccines, which have rendered most of these infectious diseases only a part of history for the citizens of the US. In fact, in the US, the Centers for Disease Control (CDC) administer the Vaccines for Children program which provided free vaccinations for approximately 40 million children in 2010. Approximately 70% of these children are enrolled in Medicaid. To prevent outbreaks of disease and reduce the costs of treating these infectious diseases, the US has made vaccination a national priority independent of economic status. Low-cost vaccines are desperately required and these vaccines are a national priority now and in the foreseeable future.

Given the importance of vaccines, the need to continually develop new and improved vaccines to improve the health of our population is clear. Even more critical is the need to provide lower cost vaccines to assist with reducing the sky-rocketing costs of the US healthcare system. A national priority is to lower the costs of the US healthcare system.

Contributing to these difficulties, even in the US, is compliance with vaccine storage requirements. A study conducted by the Office of the Inspector General at the Department of Health and Human Services (HHS) and reported in 2012 (OEI-04-10-00430) found that providers participating in the Vaccines for Children Program of the CDC: 1.) exposed vaccines to temperatures outside their approved temperature ranges; 2.) stored vaccines in refrigerators and freezers at temperatures outside their approved temperature ranges; and 3.) had expired vaccines stored with non-expired vaccines.

Another issue with vaccines is that vaccines can have a short shelf life and are prone to expire prior to use.

In addition, the study described above conducted by the Office of the Inspector General found that 16 of 46 US healthcare providers of Vaccines for Children program had expired vaccines stored with unexpired vaccines. On average, these expired vaccines had been expired for about 6 months. For example, it was reported that as of Jul. 1, 2010 40 million unused doses of swine flu vaccine that cost about $260 million to produce had just expired and were being destroyed. Vaccine expirations result in significant economic losses each year in the US.

Adjuvants enhance the immune responses to antigens of vaccines. Of the 34 vaccines provided under the Vaccines for Children Program administered by the CDC in the US, 20 contain adjuvants. Of these 20 vaccines with adjuvants, 19 of these vaccines contain alum adjuvants and 1 vaccine contains monophosphoryl lipid A adsorbed to alum (GSK's MPL) as the adjuvant.

Despite industry wide attempts at developing new adjuvants, currently only alum and GSK's MPL are used in approved vaccines in the US. Numerous adjuvant development failures have occurred in the US, but the need for new and effective adjuvants remains high.

GlaxoSmithKline's (GSK) Cervarix vaccine containing 3'-O-desacyl-4'-monophosphoryl lipid A adsorbed to alum (GSK's MPL) was licensed in the US for the prevention of cervical cancer caused by human papillomavirus. Because the starting material to produce MPL is isolated from *Salmonella minnesota*, the final product is a dynamic, complex mixture of hexa-, penta-, and tetraacyl analogues; each of these analogues differ in biological activity. As a result, the mixture of 3'-O-desacyl-4'-monophosphoryl lipid A presents manufacturing, testing, and use challenges that greatly contribute to the expense and supply issues with the vaccine.

In addition to storage problems, vaccine injections are often painful to the recipient. Redness, swelling, itching and tenderness at injection sites may occur after administration of a vaccine. The Prescribing Information of GSK's Cervarix Vaccine containing MPL and alum adjuvants lists local adverse events that may include pain, redness, and swelling. Local pain that prevented activities of daily life was reported in approximately 8 percent of subjects receiving either GSK's Cervarix vaccine or the adjuvant alum alone. Systemic adverse reactions observed after administration of vaccines containing MPL and alum adjuvants include headache, fatigue, fever, rash, myalgia, arthralgia, urticaria, and gastrointestinal symptoms including nausea, vomiting, diarrhea, and/or abdominal pain.

Furthermore, as described in the "Clinical Review of Human Papillomavirus Bivalent (Types 16 and 18) vaccine [GSK's Cervarix Vaccine], Recombinant, Biologics License Application Efficacy Supplement" four studies reported local adverse events including local pain preventing movement in approximately 16 percent of subjects. Swelling was also reported at greater than 50 mm in approximately 3 percent of subjects. The same four studies reported systemic severe adverse events in 2.4 to 7.8 percent for arthralgia, fatigue, gastrointestinal, headache, and myalgia.

The severity of the injection site reactions and systemic reactions are significant requiring medical treatment involving narcotic use, IV hydration, or other physician implemented treatments and loss of work from preventing daily activity due to diarrhea, myalgia, fatigue, headache, and vomiting.

The Advisory Committee on Immunization Practices establishes recommendations for the National Strategy for Pandemic Influenza. This strategy includes the need to "provide pandemic vaccine to all US citizens within 6 months of a pandemic declaration: pandemic vaccine (600 million doses) [National Strategy for Pandemic Influenza (November 2005) and HHS Pandemic Influenza Plan (November 2005)" and requires the use of adjuvants to attempt to move toward this seemingly unapproachable vaccination target. Since there is no approved adjuvant for a general flu vaccine in the US, the US national vaccine stockpile was without an alternative and purchased the MF59 adjuvant from Novartis for about $500 million. The MF59 adjuvant was recently discontinued in a clinical study of Fluad Paediatric due to "high vaccine reactogenicity observed in children 9 through 12 years of age, the protocol of study V7P29 was amended to exclude children less than 9 years of age." The evidence supports that during a national pandemic declaration a significant number of severe reactions will occur due to the use of the MF59 adjuvant and require additional medical care.

A synthetic analogue of monophosphoryl lipid A was introduced by Avanti Polar Lipids (Alabaster, Ala., USA) in around 2004 time period. Avanti Polar Lipids named this synthetic analogue phosphorylated hexaacyl disaccharide (PHAD), alternatively known as "GLA". PHAD supplied by Avanti Polar Lipids is provided as a single compound, shown in FIG. 1, of approximately 98% purity with a molecular weight of 1763 Daltons. PHAD's purity is in stark contrast to GSK's MPL isolated from *Salmonella minnesota* that, as described above, exists as a dynamic, complex mixture. Unlike GSK's MPL, PHAD's manufacturing process, supply, use, and stability can be closely monitored and controlled as a pure compound.

Whether or not a specific adjuvant or combination of adjuvants will enhance an immune response toward each specific antigen is unpredictable. For example, GSK's Cervarix vaccine contains both monophosphoryl lipid A and alum, because this combination is superior to alum alone (Giannini et al. Vaccine, 2006, 24, p. 5937-5949). A similar increase in efficacy was observed with a vaccine that used a recombinant hepatitis B surface antigen. (Vaccine, 1998, 16(7), p. 708-714). Another example demonstrating the variability of antigen—adjuvant combinations in producing an immune response for a specific antigen is shown in Table 6 of U.S. Pat. No. 6,889,885. These inventors demonstrated that the QS-21 adjuvant and, separately, the alum plus monophosphoryl lipid A adjuvant combination generated greater antibody responses to a 74 kD protein than alum or monophosphoryl lipid A alone. Furthermore, in 2009 Derek T. O'Hagan and Ennio De Gregorio of Novartis Vaccines published a review about the development of adjuvants. (Drug Discovery Today, 14(11/12), June 2009, p. 541-551) They reported that alum is a relatively weak adjuvant for certain proteins or antigens and new adjuvants are still required.

In 2004 the Infectious Disease Society of America (IDSA) forewarned a pending crisis of increasing antibiotic resistant bacteria throughout the world with no new antibiotics on the horizon to combat this occurrence. In 2009 the IDSA identified that bacterial infections now occur that are resistant to all current antibiotics, and that the most alarming antibiotic resistant bacteria are gram-negative bacteria including *E. coli*. In 2010, the IDSA stated that despite efforts by many private, public, and government laboratories, research had not produced any new alternatives to treat antibiotic resistant bacteria and a global commitment was now required. IDSA's urgency is supported by scientists at GlaxoSmithKline who predicted it would be greater than ten to fifteen years prior to the launch of any new antibiotics for the treatment of gram-negative bacterial infections (Payne et al. Nature Reviews Drug Discovery. 2007, 6, p. 29-40).

Their prediction was based upon the failure of 34 companies that attempted to develop new antibiotics. A consensus among the scientific community is emerging that the US urgently needs new treatments for bacterial infections. Adam L. Hersh and colleagues reported a survey with 562 infectious disease physicians responding across the US in the journal of *Clinical Infectious Disease* in 2012 (Hersh et al. *CID*. 2012. 54(11), 1677-8) that 63% of these physicians had treated patients with bacterial infections resistant to all known antibiotics within the last year. These data emphasize the need for new treatments for bacterial infections. The failure in the art to identify new therapeutic alternatives to prevent and treat gram-negative bacterial infections is well documented.

Moreover, at least five vaccines under development to prevent or treat *Staphylococcus aureus* infections have recently been discontinued. These include STAPHVAX, Veronate, Aurexis, Aurograb, and V710. The failure to identify new vaccines to prevent and treat bacterial infections is well documented.

Urinary tract infections (UTIs) are one of the most prevalent infectious diseases worldwide and the number one infectious disease suffered by women in the US. Symptoms of UTIs include dysuria (painful urination), urgency to urinate, and suprapubic pain. Acute uncomplicated UTIs occur in an estimated 7 to 11 million women in the US each year. Over half of all adult women will suffer from one or more UTIs in their lifetime with 25-44% of women experiencing a recurrent UTI. In fact, approximately 1,000,000 women and men in the US experience three or more UTI episodes per year. Moreover, recurrence often occurs within 30 to 90 days of infection despite appropriate antibiotic treatment and apparent clearance of the initial infection from the urine.

Despite recent progress in the epidemiology and pathogenesis of UTI, there have been no recent major improvements in our ability to actually prevent or treat these infections. The 25 to 44% of women with UTI who experience recurrent infections require additional treatment, additional costs, and in some cases extensive urological evaluation to prevent more severe complications from arising. Thus, safe and effective vaccines that have the potential to improve patient convenience and decrease costs are of considerable interest to patients, providers, and health care organizations. In the recurrent UTI population, antimicrobial resistance is of great concern since treatment options are diminishing. There is, therefore, an urgent need to develop new approaches to UTI prevention and treatment that depend less on the use of antimicrobials.

UTIs are most commonly caused by uropathogenic *Escherichia coli* (UPEC), which can be responsible for up to 85% of community-acquired UTIs. A critical pathogenic cascade by which UPEC evade host defenses and rapidly expand in numbers in the urinary tract to cause disease has been uncovered. This work supports the clinical need for a UTI vaccine.

FimH plays a significant role in several stages of the pathogenesis cascade, which makes it a prime vaccine target. UPEC strains that lack the FimH adhesin are unable to effectively colonize the bladder. A vaccine against FimH will activate host defenses to recognize and clear UPEC at all stages of infection, even when protected in IBCs or intracellular reservoirs.

A FimCH vaccine with MF59 as the adjuvant containing squalene was jointly invented by scientists at MedImmune, Inc. and the laboratory of Professor Scott Hultgren (U.S. Pat.

No. 6,500,434; incorporated herein in its entirety). The FimH protein and FimC protein exist as a non-covalent protein complex, FimCH. FimC stabilizes FimH and antibodies are produced against both proteins, however, only antibodies to FimH have been shown to reduce *E. coli* colonization of bladders in animals. The use of FimCH as an antigen in a vaccine is therefore limited by the requirement of an effective adjuvant.

The FimCH vaccine with the MF59 adjuvant containing squalene (an oil-in-water emulsion) elicited an immune response during Phase 1 clinical trials (United States Patent Application 20030138449; incorporated herein in its entirety.). Phase 2 clinical trials were conducted in two distinct populations again with the MF59 adjuvant containing squalene, but women did not produce relevant IgG titers to FimH in either of these trials. The development of MedImmune's FimCH vaccine with the MF59 adjuvant was discontinued because of these disappointing results. The MF59 adjuvant with squalene has a history of causing severe local injection site and systemic reactions when used with certain antigens. During these Phase 2 clinical trials, women experienced severe injection site reactions and severe systemic reactions. Because of this failure, a vaccine for the treatment or prevention of UTI does not exist in the US.

An ongoing need exists for a vaccine to prevent and treat UTI. The failure of MedImmune and others to develop a UTI vaccine evidences the difficulties of developing new vaccines for bacterial infections. MedImmune demonstrated that alum does not sufficiently enhance the immune response to FimCH. MedImmune had no clear alternatives of adjuvants to pair with the FimCH antigen.

Accordingly, there is an urgent need for vaccines, and adjuvants used to enhance the immune response to antigens in vaccines. There is a need for vaccines and adjuvants for vaccines that have extended stability without sacrificing efficacy. In particular, there is an urgent and widely recognized need in for more room temperature stable vaccines and adjuvants. In addition, it would be desirable to have vaccines, adjuvants and compositions that are stable at temperature above room temperature.

In addition there is a need for adjuvants and pharmaceutical compositions that produce less severe injection site and systemic reactions.

There is a need for new vaccines to prevent and treat bacterial infections, and for vaccines for the prevention and treatment of UTIs in particular.

It would be desirable to have vaccines, and adjuvants used to enhance the immune response of antigens in vaccines, with increased shelf-lives that can be produced in a cost effective manner. Such vaccines and adjuvants would significantly lower healthcare costs in the US, particularly if they can be stored at room temperature or greater without negatively affecting their stability.

It would be desirable to have adjuvants and vaccines that produce minimal injection site and systemic reactions. It would be desirable to have formulations with as few as excipients as possible.

It would be desirable to have a vaccine, and adjuvant for a vaccine that enhances the immune response treat bacterial infections. It would be desirable to have a vaccine, and adjuvant for a vaccine that enhances the immune response to *Escherichia coli* to patients with UTI.

BRIEF SUMMARY OF THE INVENTION

The present invention addresses many problems of prior art adjuvants, vaccines and pharmaceutical compositions described herein. The present invention provides novel liquid adjuvant compositions and formulations which provides many unexpected and advantageous properties unknown in the art of adjuvant and pharmaceutical compositions.

In one aspect, liquid adjuvant compositions and formulations that exhibit room temperature stability for about more than 6 months and up to about 37° C. for about 60 or more days is provided. The novel liquid adjuvant compositions and formulations can be stored at refrigerated or room temperature conditions facilitating its shelf life during shipping and storage and lowering its delivery costs.

The adjuvant formulations of the invention described herein address many current obstacles in vaccine administration by enabling a low cost and unexpectedly and remarkably stable adjuvant formulation which enhances an immune response to *E. coli* antigen with less severe injection site and systemic reactions.

The data described herein demonstrate that the adjuvant formulations of the invention enhance the immune response to other antigens including bacterial and viral antigens.

The invention described herein contributes to reducing this problem by treating urinary tract infections caused by gram-negative bacteria including *E. coli*.

In one aspect, a novel adjuvant composition with remarkable stability at 2° C. to 8° C. and room temperature up to about 37° C. is disclosed.

In one aspect of the invention, a composition comprising one synthetically produced adjuvant phosphorylated hexaacyl disaccharide and a buffer selected from the group consisting of citrate, succinate, and phosphate at about 25 mM to about 50 mM, preferably 28 mM to about 50 mM, and most preferably 30 mM to about 50 mM. These novel phosphorylated hexaacyl disaccharide compositions are preferably aqueous buffered suspensions. The composition can be used in a variety of ways in the vaccine and pharmaceutical context. The composition, with preferably no additional components, significantly improves the stability of phosphorylated hexaacyl disaccharide in suspension and achieves exceptional stability at room temperature and up to and at about 37° C. The compositions also exhibit excellent stability at refrigerated temperature as well. This represents a significant advancement in adjuvant and pharmaceutical technology by providing an efficient and economical phosphorylated hexaacyl disaccharide composition that does not require refrigeration for long term stability.

In another aspect of the invention, novel adjuvant formulations as an aqueous buffered suspension are provided. In one embodiment the adjuvant formulations include one synthetically produced adjuvant phosphorylated hexaacyl disaccharide, a buffer selected from the group consisting of citrate, succinate, and phosphate at about 10 mM to about 50 mM, preferably about 25 mM to about 50 mM, more preferably 28 mM to about 50 mM, and most preferably 30 mM to about 50 mM, and preferably one synthetically produced phosphatidylcholine. When a phosphatidylcholine is added, the preferred buffer concentrations can be expanded to about 10 mM to about 50 mM and achieve the remarkable stability described herein. These novel adjuvant formulations are preferably aqueous buffered suspensions. The adjuvant formulations have excellent long-term stability when stored at refrigerated and room temperatures and excellent stability up to and at about 37° C. These formulations can be produced at remarkably low costs.

The novel adjuvant formulations described herein do not require lyophilization, or equivalent process for room temperature stability or stability up to and at about 37° C. The adjuvant formulations include a specific buffer and optionally and preferably one or more synthetically produced phosphatidylcholines selected from the group consisting of DMPC, DPPC, DSPC, DOPC, and POPC, preferably DPPC, and one synthetically produced adjuvant, phosphorylated hexaacyl disaccharide, in a molar ratio of about 1:1 to 40:1 (phosphatidylcholine:phosphorylated hexaacyl disaccharide), preferably about 1:1 to 20:1 (phosphatidylcholine:phosphorylated hexaacyl disaccharide), more preferably about 2:1 to 5:1 (phosphatidylcholine:phosphorylated hexaacyl disaccharide), and most preferably about 2:1 to 5:1 (DPPC: phosphorylated hexaacyl disaccharide).

One of the most valuable aspects of the invention is that the adjuvant formulations include only a single adjuvant phosphorylated hexaacyl disaccharide in citrate, succinate or phosphate buffers at specified concentrations as described herein, and preferably a single phosphatidylcholine. No other ingredients are required to produce the unexpected long-term stability at room temperature. Further the adjuvant formulation can be produced at low cost. In this regard, the long-term stability of these adjuvant formulations at room temperature is remarkable and is achieved without the use of cholesterol, phosphatidylglycerol, phosphatidylethanolamine, monoacylglycerol, lyoprotectants, and metabolizable oil. Conventional prior art adjuvants do not achieve stability without the use of one or more of these ingredients.

Another aspect of this invention is adjuvant formulations that do not need two or more phosphatidylcholines or the addition of a phosphatidylglycerol. As shown in the examples, two or more phosphatidylcholines or one or more phosphatidylglycerols can be added to these formulations, but preferably it is not needed to achieve the remarkable long-term stability demonstrated herein.

While not bound by theory, expansion of the preferred buffer concentrations of citrate, succinate, or phosphate buffer to about 10 mM to about 50 mM to achieve the remarkable stability of the invention described herein is believed to be due to addition of preferred excipients, preferably phosphatidylcholine, at the defined molar ratio of the preferred aspect of the invention of phosphatidylcholine to phosphorylated hexaacyl disaccharide described herein. More preferably, the preferred buffer concentrations are about 25 mM to about 50 mM, even more preferably 28 mM to about 50 mM, and most preferably 30 mM to about 50 mM. Preferably the pH is in a range of about 4.0 to about 7.5, preferably about 4.5 to about 6.5, more preferably about 5.0 to 6.0.

As shown in the examples, this exceptional stability at room temperature is not present when formulated in water, acetate buffer, PBS, or citrate or phosphate buffers at or greater than 100 mM. Instead the stability is produced by citrate, succinate, or phosphate at concentrations of about 10 mM to about 50 mM, but preferably about 25 mM to about 50 mM, more preferably 28 mM to about 50 mM, and most preferably 30 mM to about 50 mM.

Another embodiment of the invention includes a non-ionic surfactant, preferably polysorbate 80, to reduce the aggregation of particles of the invention.

Removing the need for lyophilization is a significant advantage and unexpected breakthrough because many costly steps and risks have been eliminated. Another aspect of this invention is that these adjuvant formulations are superior at enhancing an immune response to an antigen while causing significantly less severe injection site and systemic reactions during administration compared to the prior art. Another aspect of this invention is adjuvant formulations substantially free of metabolizable oils, including squalene, and substantially free of cholesterol. In the art, it is widely considered that cholesterol is necessary for adjuvant formulations or liposomes to function. The current invention produces all its benefits as described herein without requiring cholesterol.

Therefore, the advantages of the adjuvant formulations and pharmaceutical compositions described herein include: room temperature stability as an aqueous buffered suspension for at least 6 months, and/or stability up to and at about 37° C. for about 60 or more days; less severe injection site and systemic reactions per administration while enhancing immune responses to antigens; and, lower cost of production or manufacturing with fewer materials or components and lower concentration of the materials or components. The inventive adjuvant formulations provide these three combined major benefits not previously achieved by adjuvants that are synthetic analogues of MLA or MPL as alternatives to alum-based adjuvants.

In another aspect of the invention novel vaccine compositions containing the novel adjuvant formulations for use to treat and prevent urinary tract infections caused by gram-negative bacteria including *Escherichia coli* and multi-drug resistant *E. coli* are provided. Methods of administration of said novel vaccine compositions and methods of treatment to prevent and treat urinary tract infections caused by gram-negative bacteria including *E. coli* and multi-drug resistant *E. coli* are also provided.

In another aspect of the invention methods of inducing the production of antibodies against FimH in a human with recurrent urinary tract infections are provided.

Another aspect of the invention is vaccine compositions that induce the production of antibodies against FimH in a human with recurrent urinary tract infections.

In another aspect of the invention, a vaccine kit comprising the phosphorylated hexaacyl disaccharide compositions or formulations or vaccine compositions, along with administration directions and instructions for storage are provided. The instructions provide for the exposure of the phosphorylated hexaacyl disaccharide compositions or formulations at room temperature and up to and about 37° C. These instructions describing storage, shipping, and exposure temperatures may be approved by a government regulatory authority including the US FDA or European Medicines Agency. Preferably, one or more of the kit components is the phosphorylated hexaacyl disaccharide compositions or formulations in a syringe.

Another aspect of the invention is that the phosphorylated hexaacyl disaccharide composition and formulations and vaccine compositions are sterile compositions and sterile pharmaceutical compositions, more preferably the sterile phosphorylated hexaacyl disaccharide compositions and formulations are contained in a sterile syringe.

DETAILED DESCRIPTION OF THE INVENTION

Definitions

"About" in reference to phosphorylated hexaacyl disaccharide quantity or buffer concentration (unless defined) means plus and minus 10% of the listed quantity.

"About 25° C." refers to temperatures at 20° C. to 30° C.

"About 37° C." refers to temperatures at 34° C. to 40° C.

"About 50 mM" refers to the buffer concentrations described herein means between 50 mM and less than 100 mM. As shown in the examples, 100 mM or greater of the specified buffers is not as effective in enabling long-term room temperature stability. The upper end of buffer concentrations is typically evaluated at two-fold increments. With reference to about 50 mM, the specified buffer concentrations of the invention are preferably less than 90 mM, preferably less than 80 mM, more preferably less than 70 mM, and most preferably less than 60 mM.

"About 10 mM" refers to the buffer concentrations described herein means between 6 mM and 10 mM.

"Acceptable carrier" refers to a carrier that is not deleterious to the other ingredients of the composition and is not deleterious to material to which it is to be applied.

"Adjuvant" refers to an agent that, when present in an effective amount, increases the antigenic response; a substance enhancing the immune response to an antigen; or an agent that stimulates antibody production to an antigen. Numerous naming conventions or terminologies exist in the art. Without reference to a specific naming convention, the adjuvant compositions as described herein may simply be referred to as adjuvant formulations or adjuvant preparations.

"Administration" refers to any means of providing a compound or composition to a subject.

"Colloid" refers to one or more chemicals, compounds, or substances microscopically dispersed throughout an aqueous buffered solution or another substance. The adjuvant formulations described herein can also be described as colloid. One example of a colloidal dispersion is Fungizone, which consists of Amphotericin B-sodium desoxycholate for parenteral administration.

"Critical micelle concentration" refers to the concentration of surfactant(s) above which micelles form and all additional surfactants added to the system go to micelles.

"DLPC" refers to 1,2-dilauroyl-sn-glycero-3-phosphocholine.

"DMPC" refers to 1,2-dimyristoyl-sn-glycero-3-phosphocholine.

"DOPC" refers to 1,2-dioleoyl-sn-glycero-3-phosphocholine.

Figure 2:
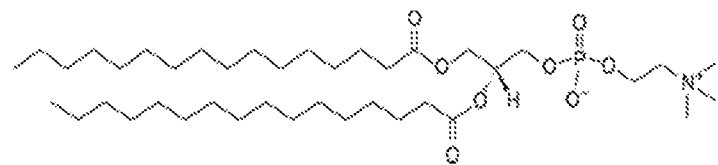
FIG. 2 shows the chemical structure of DPPC

"DPPC" refers to 1,2-dipalmitoyl-sn-glycero-3-phosphocholine (molecular formula $C_{40}H_{80}NO_8P$ (MW=734 Da) (the chemical structure is shown in FIG. 2).

"DPPG" refers to 1,2-dipalmitoyl-sn-glycero-3-phospho-(1'-rac-glycerol).

"DSPC" refers to 1,2-distearoyl-sn-glycero-3-phosphocholine.

"Effective amount" refers to a sufficient amount of FimCH or truncated FimH or other antigen in a vaccine composition that is administered to a human to elicit an immune response against FimH or other antigen, or sufficient amount of an adjuvant, preferably phosphorylated hexaacyl disaccharide, to elicit an increased immune response to antigen.

"Essentially free" in reference to materials, additives, chemicals, or excipients means the materials, additives, chemicals, or excipients have not been added to the composition or formulation of the invention, although some impurity level amounts may be present.

"Essentially free of severe injection site and systemic reactions" means two percent or less of humans experience these severe injection site and systemic reactions that are attributable to the adjuvant composition or formulation.

"Injection site reaction" refers to pain, tenderness, redness, and/or swelling at the site of administration or injection site.

"Invention" means at least some embodiments of the present invention; references to various feature(s) of the "invention" or "present invention" throughout this document do not mean that all claimed embodiments or methods include the referenced feature(s).

"Labeling" or "Label" refers to all labels and other written, printed, or graphic matter upon any article or any of its containers or wrappers, or accompanying such article and, therefore, includes any package inserts or information sheets that accompany vaccine or adjuvant compositions or formulations of the invention.

"Less severe injection site and systemic reactions" refers to less severe or Grade 3 injection site reactions and/or systemic reactions as compared to commercial vaccine Cervarix as detailed herein and in its product information documents and investigational vaccine adjuvant GLA-SE as described herein and in Treanor et al. (Vaccine 2013).

"Liposome" refers to generally vesicles that consist of a lipid bilayer membrane surrounding a hydrophilic core.

"Low cost" or "low costs" refers to a composition with the components or materials at the lowest concentrations sufficient to achieve the novel characteristics of the invention.

"Lyoprotectants" refers to materials, chemicals, or excipients primarily used to protect materials from freezing damage or other impairment during manufacturing, storage and use or improving reconstitution including enabling appropriate solvation prior to use, and also includes these materials, chemicals, or excipients used to modify osmolality or adjust tonicity, and include but not limited to sorbitol, mannitol, mannose, erythritol, xylitol, glycerol, sucrose, dextrose, trehalose, maltose, lactose, and cellobiose.

"Metabolizable oil" refers primarily to squalene, or closely related analogues of squalene as used as an adjuvant in vaccine formulations or adjuvant formulations, but also refers to medium-chain triglycerides including Miglyol 810 and oils from vegetables, animals, or fish when used in vaccine or adjuvant formulations as excipients, or to create an adjuvant effect, or to produce emulsions. Examples include grapeseed oil, soybean oil, coconut oil, olive oil, sunflower oil, corn oil, and shark liver oil.

"Micelle" refers to an aggregate of surfactant molecules dispersed in an aqueous buffered solution with the hydrophilic head regions in contact with surrounding aqueous buffered solution, sequestering the hydrophobic single-tail regions in the center of the micelle.

"MLA" refers to monophosphoryl lipid A.

"MPL" refers to 3'-O-desacyl-4'-monophosphoryl lipid A.

"Pharmaceutically acceptable carrier" refers to a carrier that is not deleterious to the other ingredients of the composition and is not deleterious to the human or other animal recipient thereof. In the context of the other ingredients of the composition, "not deleterious" means that the carrier will not react with or degrade the other ingredients or otherwise interfere with their efficacy. Interference with the efficacy of an ingredient does not, however, refer to mere dilution of the ingredient.

Figure 1:
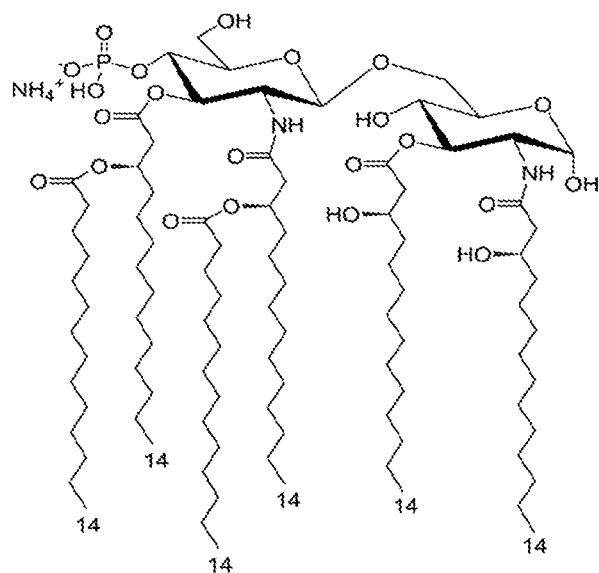
FIG. 1 shows the chemical structure of one salt of phosphorylated hexaacyl disaccharide

"Phosphorylated hexaacyl disaccharide" is a Toll-like receptor 4 agonist and refers to phosphorylated hexaacyl disaccharide or pharmaceutically acceptable salts of phosphorylated hexaacyl disaccharide. The structure of a preferred phosphorylated hexaacyl disaccharide salt is shown in FIG. 1, which is available from Avanti Polar Lipids (PHAD). Phosphorylated hexaacyl disaccharide, as used herein may be fully or partially synthetic or non-synthetic, although fully synthetic is preferred.

"Pharmaceutical composition" refers to a composition given to a mammal intended to treat or prevent a disease, or in the case of a vaccine composition, to produce an immunogenic response that treats or prevents a disease, reduce symptoms, or provides some type of therapeutic benefit, or in the case of an adjuvant composition, to enhance an immune response to one or more antigens.

"Phosphate buffer" or "phosphate" refers to a phosphate buffer selected from the following group: sodium phosphate dibasic, sodium phosphate monobasic, potassium phosphate monobasic, and potassium phosphate dibasic, or some combination thereof. Preferably "phosphate" consists of sodium phosphate dibasic, sodium phosphate monobasic, and potassium phosphate monobasic. Unless otherwise noted, reference to phosphate buffer specifically excludes ammonium phosphate.

"PBS" refers to phosphate-buffered saline of a general composition of phosphate buffer ($Na_2HPO_4$ and/or $KH_2PO_4$), potassium chloride and sodium chloride. A typical PBS composition is comprised of about 10 mM phosphate buffer ($Na_2HPO_4$ and/or $KH_2PO_4$), 2.7 mM potassium chloride and 0.14 M sodium chloride, pH 7.4, at 25° C.

"Phosphate citrate buffer" refers to a phosphate buffer containing citric acid and sodium phosphate where the pH is maintained by citrate/citric acid and phosphate/hydrogen phosphate equilibrium. The phosphate may include, for example $Na_2HPO_4$ and/or $KH_2PO_4$ and trisodium citrate may be used.

"Phosphatidylcholine" (alternatively referred to as "PC") refers to lipids containing choline. Examples include, but not limited to, DMPC (1,2-dimyristoyl-sn-glycero-3-phosphocholine), DPPC (1,2-dipalmitoyl-sn-glycero-3-phosphocholine), DSPC (1,2-distearoyl-sn-glycero-3-phosphocholine), DOPC (1,2-dioleoyl-sn-glycero-3-phosphocholine), and POPC (1-palmitoyl-2-oleoyl-sn-glycero-3-phosphocholine). Phosphatidylcholines are available from Avanti Polar Lipids.

"Phosphatidylethanolamine" refers to lipids containing a phosphate group attached to an ethanolamine, e.g. 1,2-dioleoyl-sn-glycero-3-phosphoethanolamine.

"Phosphatidylglycerol" refers to lipids containing glycerol. Examples include, but are not limited to, 1,2-dimyristoyl-sn-glycero-3-phospho-(1'-rac-glycerol) (DMPG), 1,2-dipalmitoyl-sn-glycero-3-phospho-(1'-rac-glycerol) (DPPG), and 1,2-distearoyl-sn-glycero-3-phospho-(1'-rac-glycerol) (DSPG).

"POPC" refers to 1-palmitoyl-2-oleoyl-sn-glycero-3-phosphocholine.

"Recurrent urinary tract infections" refers to a human has 3 to 4 Urinary Tract Infections in approximately one year.

"Refrigerated" refers to a temperature range from 2° C. to 8° C.

"Room temperature" refers to a range of temperature from 19° C. (66° F.) to 25° C. (77° F.).

"Saline" refers to about 125 mM to about 155 mM of NaCl in buffered aqueous solutions. For example, PBS generally contains 137 mM NaCl and Tris buffered saline may contain 150 mM.

"Severe injection site reaction" refers to one or more of the following: pain requiring narcotic pain reliever or that prevents daily activity; tenderness causing significant discomfort at rest; redness of more than 10 cm; and swelling of more than 10 cm or prevents daily activity.

"Severe systemic reaction" refers to one or more of the following: nausea/vomiting which prevents daily activity or requires outsubject IV hydration; diarrhea consisting of 6 or more watery stools or >800 grams with 24 hours or requires outsubject IV hydration; headache consisting of significant use of narcotic pain reliever or prevents daily activity; fatigue consisting of significant or prevents daily activity; and myalgia consisting of significant or prevents daily activity.

"Substantially free" in referring to cholesterol means that cholesterol, if present, is at 0.3 mM or less.

"Substantially free" in referring to monoacylglycerol means, monoacylglycerol, if present, is at 0.5 mM or less. An example of monoacylglycerol is monopalmitoyl glycerol.

"Substantially free" in referring to phosphatidylglycerol or phosphatidylethanolamine means these substances, if present, are at 0.1 mM or less.

"Substantially free" in referring to lyoprotectants means these substances, if present, are at a concentration of the composition or formulation of 0.5% or less.

"Substantially free of saline" means less than 30 mM NaCl in the composition or formulation of the invention.

"Systemic reactions" refers to nausea/vomiting, diarrhea, headache, fatigue, and/or myalgia.

"Succinate buffer" or "succinate" refers to disodium succinate or sodium succinate dibasic. Potassium succinate may be used, but is less preferred.

"Stability" or "stable" in reference to adjuvants, actives, proteins, antigens, or drugs refers to the quality of the substance or product to remain acceptable for its intended use throughout a certain time period beginning from its date of manufacture while under the influence of such variables as temperature and/or humidity. The stability of a substance is often demonstrated by analytical data (or other equivalent evidence).

"Trisodium citrate" refers to citrate buffers (also referred to as "citrate") such as, for example, trisodium citrate dihydrate, sodium citrate, sodium citrate tribasic hydrate, or citric acid trisodium salt dihydrate as referred to by suppliers including Sigma-Aldrich and BDH Chemicals. Potassium citrate, sodium citrate monobasic, and sodium citrate dibasic may be used, but they are less preferred. For example, the product imiglucerase for injection uses a combination of trisodium citrate and disodium hydrogen citrate. These types of combinations are acceptable. Citric acid, CAS 77-92-9, may be used to adjust the pH of the buffer, but it cannot substitute for the listed buffers herein.

"Truncated FimH" refers to the FimH protein truncated to include at least about 25 to about 175 amino acid residues from the first 175 amino acids of FimH. With reference to truncated FimH, the FimH protein truncated to include preferably at least 9% of the FimH protein, more preferably at least 30% of the FimH protein, and most preferably at least 60% of the FimH protein.

"Urinary Tract Infections" refers to a medical diagnosis characterized by 1 or more of the following signs and symptoms: irritative voiding such as frequency, urgency, and dysuria; gross hematuria; or elicited suprapubic tenderness upon examination; and/or 1 or more of the following laboratory results: positive urine dipstick test from clean catch or catheter urine specimen; microscopic urinalysis from clean catch or catheter urine specimen (leukocytes, bacteria, and casts may be present); or urine culture from clean catch or catheter urine specimen for *E. coli* at $\geq 10^3$ CFU/mL.

"Vaccine" or "vaccine composition" refers to a composition that improves immunity to a disease. The vaccine compositions are immunogenic compositions that elicit immune responses and antibody production toward the antigen of the composition.

EMBODIMENTS OF THE INVENTION

In one embodiment a pharmaceutical composition or pharmaceutically acceptable carrier is provided. The pharmaceutical compositions or pharmaceutically acceptable carriers are comprised of phosphorylated hexaacyl disaccharide and a buffer (referred to as "phosphorylated hexaacyl disaccharide composition" or "phosphorylated hexaacyl disaccharide containing composition" or "phosphorylated hexaacyl disaccharide containing composition and carriers"). The phosphorylated hexaacyl disaccharide compositions of the invention are preferably aqueous buffered suspensions. The buffer is selected from the group consisting of citrate, succinate, and phosphate at about 25 mM to about 50 mM, more preferably 28 mM to about 50 mM, and most preferably 30 mM to about 50 mM. Preferably the pH is in a range of about 4.0 to about 7.5, preferably about 4.5 to about 6.5, more preferably about 5.0 to about 6.0. The pharmaceutical composition or carrier with this combination (phosphorylated hexaacyl disaccharide and the buffer) demonstrates excellent stability as a base for pharmaceutical compositions and improves the overall stability of phosphorylated hexaacyl disaccharide compositions. Specifically these phosphorylated hexaacyl disaccharide containing compositions and carriers achieve stability at room temperature and up to about 37° C. These phosphorylated hexaacyl disaccharide containing compositions and carriers of the present invention also exhibit excellent long-term stability at refrigerated temperatures to room temperature.

The phosphorylated hexaacyl disaccharide containing pharmaceutical compositions and pharmaceutical carriers (which as previously described include phosphorylated hexaacyl disaccharide and a specific buffer) may optionally include other ingredients typical to vaccines, adjuvant formulations, and other pharmaceutical compositions such as excipients, modifiers, surfactants, and additives. For one example, phosphatidylcholines (as described in more detail below) may optionally be added, alone or in combination with other lipid carriers. In one embodiment naturally derived phosphatidylcholines from soy or egg or hydrogenated phosphatidylcholines from soy or egg or synthetic or natural mixed acyl phosphatidylcholines may be added.

In a preferred embodiment, one or more vaccine antigens are added to the phosphorylated hexaacyl disaccharide containing compositions to form a vaccine. The vaccine antigens may be any antigen used in vaccines including, but not limited to diphtheria, tetanus, pertussis, poliomyelitis, hepatitis, and or antigenic preparations of the influenza virus. Preferably the vaccine antigen is a FimCH protein complex as described in detail below.

The phosphorylated hexaacyl disaccharide containing compositions and carriers can be prepared at any concentration but are typically prepared at about 0.005 to about 1.0 mg/ml of phosphorylated hexaacyl disaccharide, preferably about 0.05 to 1.0 mg/ml of phosphorylated hexaacyl disaccharide, but usually not more than about 2.5 mg/ml of phosphorylated hexaacyl disaccharide.

The phosphorylated hexaacyl disaccharide containing compositions may be administered to animals or humans as an adjuvant of vaccines to preferably deliver about 10 microgram of phosphorylated hexaacyl disaccharide per dose to about 50 micrograms of phosphorylated hexaacyl disaccharide per dose. The exact dose may be modified according to the antigen used. More preferably about 20 micrograms of phosphorylated hexaacyl disaccharide per dose to about 50 micrograms of phosphorylated hexaacyl disaccharide per dose is administered. Even more preferably about 40 micrograms of phosphorylated hexaacyl disaccharide per dose to about 50 micrograms of phosphorylated hexaacyl disaccharide per dose is administered.

As shown herein, the unexpected stability of the phosphorylated hexaacyl disaccharide containing composition at room temperature and up to 37° C. is absent when formulated in water, acetate buffer, PBS, or citrate or phosphate buffers at or greater than 100 mM. The phosphorylated hexaacyl disaccharide compositions contain citrate, succinate, or phosphate buffer to produce the unexpected stability, preferably about 25 mM to about 50 mM, more preferably 28 mM to about 50 mM, and most preferably 30 mM to about 50 mM.

More particularly, preferred buffers of the phosphorylated hexaacyl disaccharide composition, the concentrations of the buffers are selected from the group consisting of about 25 mM to about 50 mM; 25 mM to about 50 mM; about 30 mM to about 50 mM; 28 mM to about 50 mM; 30 mM to about 50 mM, about 30 mM; about 40 mM to about 50 mM; 40 mM to about 50 mM; about 40 mM; and about 50 mM.

In addition, as shown in the examples below, the use of PBS in the phosphorylated hexaacyl disaccharide containing compositions and formulations do not exhibit the novel characteristics of the invention, and in particularly the stability characteristics of the invention. In contrast, the use of citrate, succinate, and phosphate buffers as specifically defined herein enables the novel stability characteristics of the invention.

The phosphorylated hexaacyl disaccharide compositions of the invention are preferably essentially free of squalene.

The phosphorylated hexaacyl disaccharide compositions of the invention are preferably essentially free of metabolizable oil used as an adjuvant.

The phosphorylated hexaacyl disaccharide compositions of the invention are preferably essentially free of metabolizable oil.

The phosphorylated hexaacyl disaccharide compositions of the invention are preferably aqueous buffered suspensions, and preferably these aqueous buffered suspensions have particle sizes less than 150 nm, even more preferably less than 130 nm, and preferably these phosphorylated hexaacyl disaccharide compositions are not oil-in-water emulsions.

The phosphorylated hexaacyl disaccharide compositions of the invention are preferably essentially free of a second adjuvant including alum, squalene, QS21, MF59, Toll-like receptor 9 agonists, and other adjuvants including squalene-based adjuvants. Second adjuvants have the potential to generate more severe local and systemic reactions in humans yet without the benefit of further increasing an immune response to improve therapeutic outcomes.

The phosphorylated hexaacyl disaccharide compositions preferably contain less than 5 mM of cholesterol, more preferably less than 1 mM of cholesterol, and even more preferably substantially free of cholesterol, and most preferably essentially free of cholesterol.

Preferably, the phosphorylated hexaacyl disaccharide compositions are substantially free of phosphatidylglycerol, and more preferably are essentially free of phosphatidylglycerol.

Preferably, the phosphorylated hexaacyl disaccharide compositions are substantially free of phosphatidylethanolamine, and more preferably essentially free of phosphatidylethanolamine.

Preferably, the phosphorylated hexaacyl disaccharide compositions are substantially free of monoacylglycerol, and more preferably essentially free of monoacylglycerol.

The phosphorylated hexaacyl disaccharide compositions are preferably substantially free of saline, preferably contain less than 20 mM NaCl, and more preferably contain less than 10 mM NaCl, and even more preferably essentially free of NaCl.

The phosphorylated hexaacyl disaccharide compositions are preferably substantially free of lyoprotectants, and even more preferably essentially free of lyoprotectants.

The phosphorylated hexaacyl disaccharide compositions do not require lyophilization, or equivalent process, to preserve the concentration of phosphorylated hexaacyl disaccharide for shelf-life or stability. Therefore, the phosphorylated hexaacyl disaccharide compositions are preferably not lyophilized or lyophilization does not occur; the phosphorylated hexaacyl disaccharide compositions are preferably not dried after preparation; the phosphorylated hexaacyl disaccharide compositions preferably do not require reconstitution from dried material with liquid or buffer after preparation; and the phosphorylated hexaacyl disaccharide compositions preferably remain as an aqueous buffered suspension after manufacturing prior to administration.

Preferably, the phosphorylated hexaacyl disaccharide compositions are substantially free of cholesterol, phosphatidylglycerol, and phosphatidylethanolamine, and essentially free of metabolizable oils and a second adjuvant.

More preferably, the phosphorylated hexaacyl disaccharide compositions are essentially free of cholesterol, phosphatidylglycerol, and phosphatidylethanolamine, and essentially free of metabolizable oils and a second adjuvant.

Preferably the phosphorylated hexaacyl disaccharide compositions of the invention are substantially free of materials or excipients as described herein that are not required to achieve the novel characteristics of the invention, but even more preferably the phosphorylated hexaacyl disaccharide compositions of the invention are essentially free of materials or excipients as described herein that are not required to achieve the novel characteristics of the invention.

Preferably the phosphorylated hexaacyl disaccharide compositions of the invention are substantially free of one, two, three, or more of materials or excipients per composition as described herein, and this limitation is not exclusive to only one material or excipient per composition.

Preferably the phosphorylated hexaacyl disaccharide compositions of the invention are essentially free of one, two, three, or more materials or excipients per composition as described herein, and this limitation is not exclusive to only one material or excipient per composition.

Preferably, when a phosphorylated hexaacyl disaccharide containing composition or formulation of the invention is stored, shipped, held, or administered at room temperature or up to about 37° C., it is most preferred to have been sterile filtered or prepared using sterile techniques, more preferably the sterile phosphorylated hexaacyl disaccharide compositions and formulations are contained in a sterile syringe.

In another embodiment novel adjuvant formulations are provided. The adjuvant formulations include one synthetically produced phosphorylated hexaacyl disaccharide, a buffer selected from the group consisting of citrate, succinate, and phosphate at about 10 mM to about 50 mM, and preferably one synthetically produced phosphatidylcholine (referred to as "phosphorylated hexaacyl disaccharide formulations" or "phosphorylated hexaacyl disaccharide containing adjuvant formulations" or "phosphorylated hexaacyl disaccharide containing formulations"). The phosphatidylcholine and phosphorylated hexaacyl disaccharide are present at a molar ratio of about 1 (PC) to 1 (phosphorylated hexaacyl disaccharide) to about 40 (PC) to 1 (phosphorylated hexaacyl disaccharide), preferably about 2.5 (PC) to 1 (phosphorylated hexaacyl disaccharide). Reference to phosphorylated hexaacyl disaccharide formulations apply to the adjuvant formulations unless otherwise noted. These novel phosphorylated hexaacyl disaccharide formulations are preferably aqueous buffered suspensions. The adjuvant formulations have excellent long-term stability when stored at refrigerated temperatures to room temperatures, and up to about 37° C. Additionally, the adjuvant formulations can be produced at low costs.

In a preferred embodiment, the adjuvant formulations include preferably one synthetically produced phosphatidylcholine, preferably DPPC, and one synthetically produced adjuvant phosphorylated hexaacyl disaccharide, in a molar ratio of about 1:1 to 40:1 (DPPC:phosphorylated hexaacyl disaccharide), and citrate, succinate, or phosphate buffers at about 10 mM to 50 mM, but preferably about 25 mM to 50 mM, more preferably 28 mM to about 50 mM, and most preferably 30 mM to about 50 mM. Preferably the pH is in a range of about 4.0 to about 7.5, preferably about 4.5 to about 6.5, more preferably about 5.0 to about 6.0. Importantly, the phosphorylated hexaacyl disaccharide adjuvant formulations can be produced with only one adjuvant phosphorylated hexaacyl disaccharide and preferably one phosphatidylcholine, thereby enabling them to be produced at low cost. Preferably, the adjuvant formulations contain phosphorylated hexaacyl disaccharide as the sole adjuvant, however additional adjuvants may be used. The long-term stability attribute of the invention further reduces costs of using these phosphorylated hexaacyl disaccharide containing adjuvant formulations.

While not bound by theory, expansion of the preferred buffer concentrations of citrate, succinate, or phosphate buffer to about 10 mM to about 50 mM in the phosphorylated hexaacyl disaccharide formulations to achieve the remarkable stability of the invention described herein is believed to be due to addition of a preferred excipient, preferably phosphatidylcholine, at the defined molar ratio of the preferred aspect of the invention phosphatidylcholine to phosphorylated hexaacyl disaccharide described herein.

The phosphorylated hexaacyl disaccharide containing adjuvant formulations of the invention are preferably essentially free of squalene.

The phosphorylated hexaacyl disaccharide containing adjuvant formulations of the invention are preferably essentially free of metabolizable oil used as an adjuvant.

The phosphorylated hexaacyl disaccharide containing adjuvant formulations of the invention are preferably essentially free of metabolizable oils.

The phosphorylated hexaacyl disaccharide containing adjuvant formulations of the invention are preferably aqueous buffered suspensions, and preferably these aqueous buffered suspensions have particle sizes less than 150 nm, even more preferably less than 130 nm, and preferably these phosphorylated hexaacyl disaccharide containing adjuvant formulations are not oil-in-water emulsions.

The phosphorylated hexaacyl disaccharide containing adjuvant formulations of the invention are preferably essentially free of a second adjuvant including alum, squalene, QS21, MF59, Toll-like receptor 9 agonists, and other adjuvants including squalene based adjuvants. The phosphorylated hexaacyl disaccharide formulations are preferably essentially free of other or additional adjuvants because they have the potential to generate more severe local and systemic reactions in humans without the benefit of further increasing an immune response or substantially improving therapeutic outcomes.

The phosphorylated hexaacyl disaccharide containing adjuvant formulations preferably contain less than 5 mM of cholesterol, more preferably less than 1 mM of cholesterol, even more preferably substantially free of cholesterol, and most preferably essentially free of cholesterol.

Preferably, the phosphorylated hexaacyl disaccharide containing adjuvant formulations are substantially free of phosphatidylglycerol, and more preferably essentially free of phosphatidylglycerol.

Preferably, the phosphorylated hexaacyl disaccharide containing adjuvant formulations are substantially free of phosphatidylethanolamine, and more preferably essentially free of phosphatidylethanolamine.

Preferably, the phosphorylated hexaacyl disaccharide containing adjuvant formulations are substantially free of monoacylglycerol, and more preferably essentially free of monoacylglycerol.

The phosphorylated hexaacyl disaccharide containing adjuvant formulations of the invention are preferably substantially free of saline, preferably contain less than 20 mM NaCl, and more preferably, the phosphorylated hexaacyl disaccharide formulations contain less than 10 mM NaCl, and even more preferably are essentially free of NaCl.

Preferably, the phosphorylated hexaacyl disaccharide containing adjuvant formulations are substantially free of lyoprotectants, and more preferably essentially free of lyoprotectants.

Preferably, the phosphorylated hexaacyl disaccharide containing adjuvant formulations are substantially free of cholesterol, phosphatidylglycerol, and phosphatidylethanolamine, and essentially free of metabolizable oils and a second adjuvant.

More preferably, the phosphorylated hexaacyl disaccharide containing formulations are essentially free of cholesterol, phosphatidylglycerol and phosphatidylethanolamine, and essentially free of metabolizable oils and a second adjuvant.

Preferably the phosphorylated hexaacyl disaccharide containing formulations of the invention are substantially free of materials or excipients as described herein that are not required to achieve the novel characteristics of the invention, but even more preferably the phosphorylated hexaacyl disaccharide containing formulations of the invention are essentially free of materials or excipients as described herein that are not required to achieve the novel characteristics of the invention.

Preferably the phosphorylated hexaacyl disaccharide containing formulations of the invention are substantially free of one, two, three, or more of materials or excipients per phosphorylated hexaacyl disaccharide containing formulation as described herein, and this limitation is not exclusive to only one material or excipient per phosphorylated hexaacyl disaccharide containing formulation.

Preferably the phosphorylated hexaacyl disaccharide containing formulations of the invention are essentially free of one, two, three, or more materials or excipients per phosphorylated hexaacyl disaccharide containing formulation described herein, and this limitation is not exclusive to only one material or excipient per phosphorylated hexaacyl disaccharide containing formulation. In another aspect, vaccines, and methods of treating and preventing disease with vaccines, are provided.

To prepare the vaccines, one or more vaccine antigens are added to the phosphorylated hexaacyl disaccharide containing adjuvant formulations described above. The antigens may be a FimCH protein complex as described herein or other antigens including, but not limited to antigens associated with diphtheria, tetanus, pertussis, poliomyelitis, hepatitis, and or antigenic preparations of the influenza virus.

A vaccine prepared using the phosphorylated hexaacyl disaccharide formulation does not require lyophilization to preserve the concentration of phosphorylated hexaacyl disaccharide for shelf-life or stability. Lyophilization is a dehydration process or freeze-drying process primarily utilized to preserve materials. Equivalent processes exist to accomplish the same goal to preserve materials. A vaccine or adjuvant formulation that does not need lyophilization is an unexpected and significant advantage in the preparation of vaccines and the phosphorylated hexaacyl disaccharide compositions described herein. By eliminating the need for lyophilization, many costly steps are eliminated. First, the lyophilization step itself is eliminated, which not only removes a costly manufacturing step that must occur under well-monitored sterile conditions, but also eliminates the validation and review of this manufacturing step. Next, the removal of the step represents an ongoing cost saving. For example, each time a lot is prepared a lyophilization step is saved. In addition, removing this step saves extra validation steps when larger batches are prepared or the manufacturing procedure is transferred to another facility. Second, lyophilization requires that a sterile vial of diluent be manufactured or procured, shipped, and stored with the lyophilized product for reconstitution. Eliminating the reconstitution step removes the cost of this diluent vial and its supply chain management. Third, the reconstitution of adjuvant formulations can compromise its sterility, necessitating its immediate use or waste of the product if not used in a pre-established amount of time. Fourth, the reconstitution process is prone to errors, so the manufacturer loses control of the exact concentration of the product that is ultimately administered to a patient. The adjuvant compositions and formulations described herein have eliminated these four disadvantages by removing the lyophilization requirement. Therefore, the phosphorylated hexaacyl disaccharide containing formulations are preferably not lyophilized or lyophilization does not occur; the phosphorylated hexaacyl disaccharide containing formulations are preferably not dried after preparation; the phosphorylated hexaacyl disaccharide containing formulations preferably do not require reconstitution from dried material with liquid or buffer after preparation; and the phosphorylated hexaacyl disaccharide containing formulations preferably remain as an aqueous buffered suspension after manufacturing prior to administration.

A further remarkable advantage of the invention described herein is now realized. Without a need for lyophilization or equivalent process, the phosphorylated hexaacyl disaccharide compositions or phosphorylated hexaacyl disaccharide containing formulations of the invention can be efficiently and cost effectively packaged into syringes immediately after manufacturing. Preferably the compositions and formulations are sterile and preferably the syringes are sterile. These prefilled syringes can be shipped, stored, delivered, or transferred at refrigerated temperatures to room temperatures and up to about 37° C. This advantage provides the most efficient and cost effective means to get phosphorylated hexaacyl disaccharide compositions and phosphorylated hexaacyl disaccharide containing formulations to a site for administration.

In another embodiment, a non-ionic surfactant is added to the adjuvant formulation. Preferably the non-ionic surfactant is polysorbate 80 although others may be used. The non-ionic surfactant is typically added at a concentration of about 0.001% to 1.0%, preferably 0.01% to 0.1%, to the adjuvant composition. This addition can prevent slight aggregation or slight increase in mean particle size of the phosphorylated hexaacyl disaccharide formulations while being stored at room temperatures and up to about 37° C. Preferably, non-ionic surfactants are derived from polyethoxylated sorbitan and include but are not limited to polysorbate 20 and polysorbate 80.

Preferred adjuvant formulations comprise a specific buffer selected from the group consisting of citrate, succinate, and phosphate at about 25 mM to about 50 mM, more preferably 28 mM to about 50 mM, and most preferably 30 mM to about 50 mM, and preferably one synthetically produced phosphatidylcholine selected from the group consisting of DMPC, DPPC, DSPC, DOPC, and POPC, preferably DPPC, and one synthetically produced adjuvant, phosphorylated hexaacyl disaccharide, in a molar ratio of about 1:1 to 40:1 (phosphatidylcholine:phosphorylated hexaacyl disaccharide), preferably about 1:1 to 20:1 (phosphatidylcholine:phosphorylated hexaacyl disaccharide), more preferably about 2:1 to 5:1 (phosphatidylcholine:phosphorylated hexaacyl disaccharide), and most preferably about 2:1 to 5:1 (DPPC:phosphorylated hexaacyl disaccharide). More preferably, citrate or succinate buffers are used in the phosphorylated hexaacyl disaccharide formulations at about 10 mM to about 50 mM, preferably at about 25 mM to about 50 mM, more preferably 28 mM to about 50 mM, and most preferably 30 mM to about 50 mM.

As described herein referring to the concentrations of the preferred buffers of the phosphorylated hexaacyl disaccharide formulation, the concentrations of the buffers are selected from the group consisting of about 10 mM to about 50 mM; 15 mM to about 50 mM; 20 mM to about 50 mM; about 25 mM to about 50 mM; 25 mM to about 50 mM; about 30 mM to about 50 mM; 28 mM to about 50 mM; 30 mM to about 50 mM, about 30 mM; about 40 mM to about 50 mM; 40 mM to about 50 mM; about 40 mM; and about 50 mM. The phosphorylated hexaacyl disaccharide containing formulations described herein are preferably substantially free of saline, preferably contain less than 20 mM NaCl, and more preferably, the phosphorylated hexaacyl disaccharide compositions contain less than 10 mM NaCl and even more preferably essentially free of NaCl.

In addition, as shown in the examples below, the use of PBS in the phosphorylated hexaacyl disaccharide containing compositions and formulations do not exhibit the novel characteristics of the invention, and in particularly the stability characteristics of the invention. In contrast, the phosphate buffers as specifically defined herein do enable the novel characteristics of the invention.

The phosphorylated hexaacyl disaccharide formulations are preferably prepared by selecting a single phosphatidylcholine prepared synthetically with high purity. However, naturally derived phosphatidylcholines from soy or egg or hydrogenated phosphatidylcholines from soy or egg or synthetic or natural mixed acyl phosphatidylcholines may also be used to prepare the adjuvant formulations.

The phosphorylated hexaacyl disaccharide formulations can be prepared at any concentration but are typically prepared at about 0.005 to about 1.0 mg/ml of phosphorylated hexaacyl disaccharide, preferably 0.05 to about 1.0 mg/ml of phosphorylated hexaacyl disaccharide, but preferably not more than about 2.5 mg/ml of phosphorylated hexaacyl disaccharide. The phosphatidylcholine of the phosphorylated hexaacyl disaccharide formulation can be prepared at any concentration, but is preferably prepared at about 0.005 to about 16 mg/mL (0.007 mM to 22 mM), more preferably about 0.05 to about 8 mg/ml (0.07 mM to 11 mM), and even more preferably about 0.05 to about 0.8 mg/ml (0.07 mM to 1 mM).

The phosphorylated hexaacyl disaccharide formulations of the invention are prepared as follows to produce a molar ratio of about 40:1 to about 1:1 of phosphatidylcholine to phosphorylated hexaacyl disaccharide, preferably DPPC to phosphorylated hexaacyl disaccharide, preferably about 2.5:1 DPPC to phosphorylated hexaacyl disaccharide. phosphorylated hexaacyl disaccharide is weighed out into an appropriate glass vial, such as a Type 1 Plus Schott glass vial. An appropriate amount of phosphatidylcholine, preferably DPPC, in ethanol is added. This preparation is sonicated for approximately 1 minute while gently swirling the preparation, and then the ethanol is appropriately removed via evaporation. The film is reconstituted with citrate, succinate or phosphate buffer, preferably 10 mM to about 50 mM trisodium citrate, pH 6.0, and sonicated at approximately 50° C. to 65° C., preferably 55° C., for approximately 30 minutes, and more than one cycle of sonication can be performed, as preferred. The prepared phosphorylated hexaacyl disaccharide formulation typically has particles sizes from about 60 nm to about 500 nm. To enable sterile filtration, the phosphorylated hexaacyl disaccharide formulation is preferably further processed to achieve a reduced and appropriate homogenous particle size, preferably between about 70 nm to 130 nm. The phosphorylated hexaacyl disaccharide formulations are extruded through an 80 nm pore polycarbonate membrane (Avestin, LFLM-80) with an Avestin extruder, or equivalent, for about 7 to about 12 passes at about 45° C. to 65° C., preferably 55° C. to achieve a homogenous particle size below about 130 nm. To ensure an acceptable recovery after sterile filtration, preferably the particle sizes of the phosphorylated hexaacyl disaccharide formulations are 150 nm or less, but even more preferably 130 nm or less.

The phosphorylated hexaacyl disaccharide formulations may optionally then be diluted with citrate, succinate or phosphate buffer at concentrations described herein, but preferably at about 25 mM to about 50 mM, more preferably 28 mM to about 50 mM, and most preferably 30 mM to about 50 mM, pH 6.0, containing an appropriate amount of polysorbate 80 to achieve a final concentration of preferably 0.02% of polysorbate 80, but 0.01% to 0.1% polysorbate 80 is acceptable. Typically, the phosphorylated hexaacyl disaccharide formulations will be diluted to about a concentration of 0.05 mg/ml to 0.5 mg/mL. The phosphorylated hexaacyl disaccharide formulations are then sterile filtered through a 0.2 um filter, preferably Sartorius. The phosphorylated hexaacyl disaccharide and adjuvant formulations of the invention described herein exhibit zeta potentials of about −20 mV to −80 mV.

The phosphorylated hexaacyl disaccharide formulations described herein, in one embodiment are used in the preparation of vaccines and are administered to animals and humans as an adjuvant of vaccines. Preferably, the formulations are designed to deliver about 10 micrograms of phosphorylated hexaacyl disaccharide per dose to about 50 micrograms of phosphorylated hexaacyl disaccharide per dose, preferably about 20 micrograms of phosphorylated hexaacyl disaccharide per dose to about 50 micrograms of phosphorylated hexaacyl disaccharide per dose, and even more preferably about 40 micrograms of phosphorylated hexaacyl disaccharide per dose to about 50 micrograms of phosphorylated hexaacyl disaccharide per dose.

In a preferred embodiment, phosphorylated hexaacyl disaccharide is provided as a single compound of approximately 98% purity with a molecular weight of 1763 Daltons (the structure of which is shown in FIG. 1). One source for the preferred phosphorylated hexaacyl disaccharide is Avanti Polar Lipids (Alabaster, Ala., USA)(PHAD). The phosphorylated hexaacyl disaccharide compositions of the present invention, however, encompass phosphorylated hexaacyl disaccharide or pharmaceutically acceptable salts of phosphorylated hexaacyl disaccharide. The phosphorylated hexaacyl disaccharide used in the compositions may be fully or partially synthetic or non-synthetic, although fully synthetic is preferred.

In other embodiments, derivatives of phosphorylated hexaacyl disaccharide, such as Monophosphoryl 3-Deacyl Lipid A (available from Avanti Polar Lipids; referred to as 3D-phosphorylated hexaacyl disaccharide) are used alone or in combination with phosphorylated hexaacyl disaccharide in the compositions and formulations of the present invention.

PHAD's purity is in stark contrast to GSK's monophosphoryl lipid A isolated from *Salmonella minnesota* that exists as a dynamic, complex mixture of hexa-, penta-, and tetraacyl analogues; each of these analogues differ in biological activity. Those skilled in the art of drug and vaccine development know that PHAD is superior to GSK's monophosphoryl lipid A because PHAD's manufacturing process, supply, use, and stability can be closely monitored and controlled as a pure compound.

The concentration of citrate, succinate, or phosphate buffer is used to improve stability of the phosphorylated hexaacyl disaccharide formulation at room temperature and up to about 37° C. While not bound by theory, it is believed that a synergistic effect results from composition of molar ratio of PC:phosphorylated hexaacyl disaccharide, which is a preferred combination, and citrate, succinate, or phosphate buffers within a specific concentration range as described herein.

Importantly, the phosphorylated hexaacyl disaccharide formulations are preferably formulated to be substantially free of various excipients or chemicals. Therefore, the addition of cholesterol or two or more phosphatidylcholines or one or more phosphatidylglycerols is not required, and preferably not included in the formulations of the invention. Adjuvant formulations essentially free of metabolizable oils, including squalene, and substantially free of cholesterol are preferred. In addition, while the prior art suggests cholesterol is a necessary chemical required for liposomes or adjuvant formulations, the adjuvant formulations described herein do not require cholesterol for the adjuvant to provide all the significant advantages over prior art formulations, and preferably no cholesterol is added to the adjuvant formulations. As shown in the Examples, two or more phosphatidylcholines or one or more phosphatidylglycerols (for a total of two or more phosphatidylcholines or phosphatidylglycerols) may optionally be added to the formulations at minor concentrations, but these are unnecessary and not required to achieve stability at room temperature or up to about 37° C. of the invention or to prevent, lower, or reduce severe injection site and systemic reactions while enhancing an immune response.

As detailed herein, those skilled in the art have been working with liposomes and other various formulations containing MLA, MPL, or synthetic analogues of these adjuvants for more than twenty years and have been unable to produce a formulation that allows for stability as described herein while in aqueous suspensions. Room temperature and up to about 37° C. stability for vaccine adjuvants is a highly sought after goal by those skilled in the art. Despite the efforts, no formulations to keep MLA, MPL, or synthetic analogues stable at the temperatures and for the time periods described herein have been developed. The invention described herein solves this problem.

Preparation of Vaccines

Another embodiment of this invention further describes novel vaccine compositions comprising the adjuvant or phosphorylated hexaacyl disaccharide formulations and FimCH or truncated FimH. Such vaccines are used to treat and prevent urinary tract infections caused by gram-negative bacteria including *Escherichia coli* and multi-drug resistant *E. coli*. FimCH is a non-covalent complex of FimC and FimH recombinant proteins. A vaccine of FimCH and phosphorylated hexaacyl disaccharide formulation is prepared by adding a predetermined volume of a phosphorylated hexaacyl disaccharide formulation to a vial of FimCH.

The following is an example of a vaccine prepared in accordance to the invention. Generally, to prepare a vaccine for administration, an effective amount of an antigen of FimCH or truncated FimH is combined with an adjuvant formulation containing about 0.005 mg/ml to about 0.5 mg/ml of phosphorylated hexaacyl disaccharide to administer about 10 µg to about 50 µg of phosphorylated hexaacyl disaccharide per injection to a human.

In practice, the following is an example of one procedure that may be used by medical personnel to prepare and administer a vaccine in accordance with the invention. The conditions and procedures are exemplary and do not limit the scope of the invention.

A vial of FimCH vial is removed from storage of about −20° C. and allowed to stand at room temperature for approximately twenty minutes to reach approximate room temperature. After the FimCH vial reaches approximately room temperature, the vial is inverted a number of times to mix the contents. Separately, a vial containing the phosphorylated hexaacyl disaccharide formulation is removed from a storage container from 2° C. to 8° C. storage. The vial of phosphorylated hexaacyl disaccharide formulation is inverted a number of times to mix the contents, and then about 0.2 mL is withdrawn with a sterile 1.0 mL syringe and injected into the FimCH vial through the stopper. Again the vial is inverted a number of times to mix the contents. Sterile water for injection (WFI) or more preferably preferred sterile buffer of the invention is withdrawn in an amount of 0.2 mL using a sterile 1.0 mL syringe and injected into the FimCH/phosphorylated hexaacyl disaccharide vial through the stopper. Again the vial is inverted a number of times. Finally, about 0.3 mL of prepared FimCH/phosphorylated hexaacyl disaccharide vaccine using a sterile 1.0 mL syringe is withdrawn. The prepared vaccine contains 50 µg of FimCH and 20 µg of phosphorylated hexaacyl disaccharide per a 0.3 mL dose. This prepared vaccine can be stored at refrigerated or room temperatures prior to administration.

In general FimCH is stored at −70° C., −20° C., or 2° C. to 8° C. for long time periods, or even room temperature for a short time period of about 4 days to two to three weeks. Typically, only sterile products should be stored at room temperature because if the products are not sterile, microbial growth is possible, but not guaranteed. The vaccine is preferably administered by intramuscular injection. Typically, about 5 micrograms of FimCH to about 200 micrograms of FimCH would be administered to a human, preferably about 20 micrograms to about 110 micrograms. Typically, about 10 micrograms of phosphorylated hexaacyl disaccharide per dose to about 50 micrograms of phosphorylated hexaacyl disaccharide per dose would be administered with FimCH, more preferably about 20 micrograms of phosphorylated hexaacyl disaccharide per dose to about 50 micrograms of phosphorylated hexaacyl disaccharide per dose, even more preferably about 40 micrograms of phosphorylated hexaacyl disaccharide per dose to about 50 micrograms of phosphorylated hexaacyl disaccharide per dose although more or less may be used. Typically, three to four doses of FimCH with the phosphorylated hexaacyl disaccharide formulation is administered to a patient in need. These doses typically occur at day 0 and then about days 30 to 60, then about 90 to 180 days, and then, if preferred, about 180 to 360 days from the first administration. As needed, additional injections may occur 12 to 36 months after the initial vaccination.

As described above, the more preferable aspect of the invention is that the phosphorylated hexaacyl disaccharide compositions and formulations are stored separately from the antigen or FimCH because the phosphorylated hexaacyl disaccharide compositions and formulations have excellent stability, and formulated or mixed appropriately with the antigen or FimCH sometime before administration to a patient or human. However, other methods of mixing, preparing and administering vaccines are possible and will function effectively.

The data in the following sections demonstrates that the adjuvant formulations of the invention enhance the immune response of other antigens including bacterial and viral antigens. One or more vaccine antigens may be added to the phosphorylated hexaacyl disaccharide formulations prepared in accordance with the invention. These antigens may be the FimCH protein complex as described herein or other antigens including, but not limited to diphtheria, tetanus, pertussis, poliomyelitis, hepatitis, and or antigenic preparations of the influenza virus.

In another embodiment, methods of administration of the novel vaccine compositions comprising adjuvant or phosphorylated hexaacyl disaccharide formulations and FimCH or truncated FimH are provided. Particularly, methods of treatment to prevent and treat urinary tract infections caused by gram-negative bacteria including E. coli and multi-drug resistant E. coli are provided. Typically, about 5 micrograms of FimCH to about 200 micrograms of FimCH would be administered to a human, preferably about 20 micrograms to about 110 micrograms. Typically, about 10 micrograms of phosphorylated hexaacyl disaccharide per dose to about 50 micrograms of phosphorylated hexaacyl disaccharide per dose would be administered, preferably about 20 micrograms of phosphorylated hexaacyl disaccharide per dose to about 50 micrograms of phosphorylated hexaacyl disaccharide per dose, even more preferably about 40 micrograms of phosphorylated hexaacyl disaccharide per dose to about 50 micrograms of phosphorylated hexaacyl disaccharide per dose. Other dosage amounts and regimens may be used dependent on the antigen used and the condition being treated.

In another embodiment, methods of inducing the production of antibodies against FimH in a human with recurrent urinary tract infections are provided.

In another embodiment, vaccine compositions that induce the production of antibodies against FimH in a human with recurrent urinary tract infections are provided.

In another embodiment, sterile compositions and sterile pharmaceutical compositions containing phosphorylated hexaacyl disaccharide are provided; preferably these compositions of aqueous buffered suspensions have particle sizes less than 150 nm, even more preferably less than 130 nm. The sterile phosphorylated hexaacyl disaccharide compositions and formulations are stored in a pharmaceutical container which is in direct contact to the phosphorylated hexaacyl disaccharide compositions and formulations. Examples of these pharmaceutical containers are vials or syringes, more preferably the sterile phosphorylated hexaacyl disaccharide compositions and formulations are contained in a sterile syringe. These pharmaceutical containers holding the phosphorylated hexaacyl disaccharide composition or formulation can be stored in a temperature-validated container, e.g. incubator, at room temperature. These pharmaceutical containers holding the sterile phosphorylated hexaacyl disaccharide composition formulation can be added to a shipping container assembled to be transferred to another location at room temperature or up to about 37° C. These shipping containers can be transferred via a government postal service or a commercial shipping service. Due to the remarkable stability of the inventions described herein, the location receiving said phosphorylated hexaacyl disaccharide compositions and formulations may be a location without refrigeration or intermittent access to refrigeration or a location without electricity or with intermittent electricity.

In another embodiment, a vaccine kit comprising the phosphorylated hexaacyl disaccharide or adjuvant compositions or formulations or vaccine composition is provided. The kit may optionally include methods of preparing and administering the vaccine and/or instructions for storage and exposure of the phosphorylated hexaacyl disaccharide compositions or formulations at room temperature and up to and about 37° C. These instructions describing storage, shipping, and exposure temperatures may be approved by a government regulatory authority including the US FDA or European Medicines Agency. Preferably, one or more of the kit components is the phosphorylated hexaacyl disaccharide compositions or formulations in a syringe. Preferably the phosphorylated hexaacyl disaccharide compositions or phosphorylated hexaacyl disaccharide containing formulations are sterile and are in a sterile syringe.

The kit may include a label for the phosphorylated hexaacyl disaccharide or adjuvant compositions or formulations of the invention providing instructions or limitations for storage and exposure of the phosphorylated hexaacyl disaccharide compositions or formulations at room temperature and up to and about 37° C. The labels or instructions describing storage, shipping, and exposure temperatures may be approved by a government regulatory authority including the US FDA or European Medicines Agency.

As stated herein, the novel characteristics of the invention enable the phosphorylated hexaacyl disaccharide compositions and formulations to be manufactured, tested, analyzed, stored, shipped, held, moved, transferred, or administered at refrigerated temperatures, room temperature, up to and about 37° C., temperatures between refrigerated temperatures and room temperature for periods of time as described herein. Due to the remarkable stability of the inventions described herein, the location receiving said phosphorylated hexaacyl disaccharide compositions and formulations may be a location without refrigeration or intermittent access to refrigeration or a location without electricity or with intermittent electricity.

EXAMPLES

Certain specific aspects and embodiments of the present disclosure will be explained in more detail with reference to the following examples, which are provided solely for purposes of illustration and are not to be construed as limiting the scope of the disclosure in any manner. The amounts used do not represent a limitation and the process can be scaled up to produce larger batches Example 1

Phosphorylated hexaacyl disaccharide formulations are manufactured as follows to produce a molar ratio of about 2.5:1 of DPPC to phosphorylated hexaacyl disaccharide.

PHAD Avanti Polar Lipids (Alabaster, Ala., USA), phosphorylated hexaacyl disaccharide, and DPPC can be obtained from Avanti Polar Lipids (Alabaster, Ala., USA) as either non-GMP or GMP material (the Certificate of Analysis is provided in Table 1). PHAD is a synthetic version of monophosphoryl lipid A. PHAD is formulated with DPPC to prepare the adjuvant formulation of the invention. DPPC's release specifications are provided in the table 2. The transition temperature of DPPC is 41° C.

PHAD is weighed out into an appropriate glass vial, preferably a Type 1 Plus Schott glass vial. An appropriate amount of an approximately 2.3 mg/ml DPPC solution, or equivalent, in ethanol is added. This preparation is sonicated for approximately 1 minute while gently swirling the preparation, and then the ethanol is appropriately removed via evaporation using care. The film is reconstituted with 10 mM trisodium citrate, pH 6.0, and sonicated at approximately 50° C. to 65° C., preferably 55° C., for approximately 30 minutes. The phosphorylated hexaacyl disaccharide formulations are typically prepared at about 0.5 to 1.0 mg/ml, but not more than about 2.5 mg/ml. (As described herein, molar ratios of for example about 13:1 DPPC:phosphorylated hexaacyl disaccharide can also be prepared using this same procedure by adjusting the amount of DPPC as needed.

The prepared PHAD formulations typically exhibit particles sizes from about 60 nm to about 500 nm. To enable sterile filtration, the PHAD formulations have to be further processed to achieve a reduced and appropriate homogenous particle size, typically between about 70 nm to 130 nm. Even though numerous literature references, including U.S. Pat. No. 6,630,161, report high-pressure homogenization is a preferred method to reduce the particle size of liposomes, high-pressure homogenization using an Avestin homogenizer of pressures up to 25,000 psi do not significantly or relevantly reduce the particle sizes of these PHAD formulations. This difficulty was unexpected. These PHAD formulations must be extruded through an 80 nm pore polycarbonate membrane (Avestin, LFLM-80) with an Avestin extruder, or equivalent, for about 7 to about 12 passes at about 45° C. to 65° C., preferably 55° C. to achieve a homogenous particle size below about 130 nm. Extruding at 45° C. to 65° C. is an important parameter. To ensure an acceptable recovery after sterile filtration, the particle sizes of the phosphorylated hexaacyl disaccharide adjuvant formulations are preferably 150 nm or less, but more preferably 130 nm or less.

The phosphorylated hexaacyl disaccharide formulations may then be diluted with 10 mM trisodium citrate, pH 6.0 containing an appropriate amount of polysorbate 80 to achieve a final concentration of most preferably 0.02% of polysorbate 80, but 0.01% to 0.1% polysorbate 80 is acceptable. Typically phosphorylated hexaacyl disaccharide formulations will be diluted to about a concentration of 0.05 mg/ml to 0.5 mg/mL. These phosphorylated hexaacyl disaccharide formulations are then sterile filtered through a 0.2 um filter, preferably Sartorius.

As determine by cryogenic transmission electron microscopy, the adjuvant formulations described herein are suspensions.

Additional or alternative steps may be added to the procedure above to prepare the phosphorylated hexaacyl disaccharide formulations. For one example, the ethanol may be evaporated by rotary evaporation, or equivalent, or via a nitrogen stream, or equivalent. For another example, the sonication step including a buffer of the invention may be repeated two or more times, the formulation may be cooled to room temperature or less between repeated sonications, and the formulation may be held at a temperature similar to the sonication step for one or more hours before, during, or after said sonication.

TABLE 1

Certificate of Analysis Information for PHAD from Avanti Polar Lipids, Inc.

| Analysis | Specification | Results |
|---|---|---|
| Physical examination | White to off-white powder or lyophilized cake which contains no foreign matter. | Pass |
| TLC (65:25:4 (v/v/v) chloroform:methanol:water) | Ninhydrin spray, negative Iodine, 1 major spot Phosphorus spray, positive Charring, positive Water dip, 1 major spot Rf consistent with structure | All pass |
| HPLC | NLT 97% purity | 99.2% |
| Proton NMR | Consistent with structure | Consistent with structure |
| Phosphorus NMR | Consistent with structure | Consistent with structure |
| MS | Consistent with structure (exact mass = 1762.3) | Consistent with structure |
| Karl Fischer Water Titration | NMT 5% water | 1.4% |
| Residual Solvents (GC/FID)* | NMT 2000 ppm methanol NMT 2000 ppm ethanol NMT 2000 ppm acetone NMT 200 ppm hexane NMT 2000 ppm cyclohexane NMT 500 ppm toluene NMT 50 ppm chloroform/ethyl acetate NMT 5000 ppm total residual solvents | None Detected None Detected None Detected None Detected None Detected None Detected None Detected |
| Palladium (ICPMS)* | NMT 10 ppm | <0.1 ppm |
| Heavy Metals Screen + Ruthenium + Iridium by ICPMS* | NMT 20 ppm | <20 ppm |

TABLE 2

Certificate of Analysis Information for DPPC from Avanti Polar Lipids, Inc.

| Analysis | Specification | Results |
|---|---|---|
| Physical examination | White solid which contains no foreign matter. | Pass |
| TLC | Ninhydrin spray, negative Iodine, 1 major spot Phosphorus spray, positive Charring, negative Water dip, 1 major spot Rf consistent with structure | All Pass |
| Quantitative Phosphorus NMR | NMT 1% 16:0 dimethyl PE | None detected |
| HPLC | NMT 1% palmitic acid NMT 1% 16:0 lyso PC NLT 99% purity | None detected 0.7% 99.3% |
| Fatty acid methyl ester by GC/FID | NLT 99% (AUC) palmitoyl methyl ester | 100.0% |
| Karl Fischer Water Titration | NMT 8% water | 0.5% |
| Residual Solvents by | NMT 100 ppm methanol | None Detected |

TABLE 2-continued

Certificate of Analysis Information for DPPC from Avanti Polar Lipids, Inc.

| Analysis | Specification | Results |
|---|---|---|
| GC/FID | NMT 100 ppm ethanol | None Detected |
| | NMT 100 ppm acetone | None Detected |
| | NMT 100 ppm hexane | None Detected |
| | NMT 100 ppm cyclohexane | None Detected |
| | NMT 100 ppm toluene | None Detected |
| | NMT 20 ppm chloroform | None Detected |
| | NMT 250 ppm total residual solvents | None Detected |

Example 2

Antigens for the vaccine may be prepared as follows.

FimCH is a non-covalent complex of FimC and FimH recombinant proteins. The recombinant proteins are derived from transgenic E. coli culture. The FimC and FimH proteins are expressed separately in E. coli, and they spontaneously form a non-covalent complex. The molecular weight of the FimCH complex is approximately 51,700 Daltons.

The FimH protein (SEQ ID No: 1) of the complex has a molecular weight of 29,065 Daltons, and it consists of 279 amino acid residues represented by the sequence below:

Phe Ala Cys Lys Thr Ala Asn Gly Thr Ala Ile Pro Ile Gly Gly Gly Ser Ala Asn Val Tyr Val Asn Leu Ala Pro Val Val Asn Val Gly Gln Asn Leu Val Val Asp Leu Ser Thr Gln Ile Phe Cys His Asn Asp Tyr Pro Glu Thr Ile Thr Asp Tyr Val Thr Leu Gln Arg Gly Ser Ala Tyr Gly Gly Val Leu Ser Asn Phe Ser Gly Thr Val Lys Tyr Ser Gly Ser Ser Tyr Pro Phe Pro Thr Thr Ser Glu Thr Pro Arg Val Val Tyr Asn Ser Arg Thr Asp Lys Pro Trp Pro Val Ala Leu Tyr Leu Thr Pro Val Ser Ser Ala Gly Gly Val Ala Ile Lys Ala Gly Ser Leu Ile Ala Val Leu Ile Leu Arg Gln Thr Asn Asn Tyr Asn Ser Asp Asp Phe Gln Phe Val Trp Asn Ile Tyr Ala Asn Asn Asp Val Val Val Pro Thr Gly Gly Cys Asp Val Ser Ala Arg Asp Val Thr Val Thr Leu Pro Asp Tyr Arg Gly Ser Val Pro Ile Pro Leu Thr Val Tyr Cys Ala Lys Ser Gln Asn Leu Gly Tyr Tyr Leu Ser Gly Thr His Ala Asp Ala Gly Asn Ser Ile Phe Thr Asn Thr Ala Ser Phe Ser Pro Ala Gln Gly Val Gly Val Gln Leu Thr Arg Asn Gly Thr Ile Ile Pro Ala Asn Asn Thr Val Ser Leu Gly Ala Val Gly Thr Ser Ala Val Ser Leu Gly Leu Thr Ala Asn Tyr Ala Arg Thr Gly Gly Gln Val Thr Ala Gly Asn Val Gln Ser Ile Ile Gly Val Thr Phe Val Tyr Gln

The FimC (SEQ ID No: 2) protein of the complex has a molecular weight of 22,700 Daltons, and it consists of 205 amino acid residues represented by the following sequence:

Gly Val Ala Leu Gly Ala Thr Arg Val Ile Tyr Pro Ala Gly Gln Lys Gln Val Gln Leu Ala Val Thr Asn Asn Asp Glu Asn Ser Thr Tyr Leu Ile Gln Ser Trp Val Glu Asn Ala Asp Gly Val Lys Asp Gly Arg Phe Ile Val Thr Pro Pro Leu Phe Ala Met Lys Gly Lys Lys Glu Asn Thr Leu Arg Ile Leu Asp Ala Thr Asn Asn Gln Leu Pro Gln Asp Arg Glu Ser Leu Phe Trp Met Asn Val Lys Ala Ile Pro Ser Met Asp Lys Ser Lys Leu Thr Glu Asn Thr Leu Gln Leu Ala Ile Ile Ser Arg Ile Lys Leu Tyr Tyr Arg Pro Ala Lys Leu Ala Leu Pro Pro Asp Gln Ala Ala Glu Lys Leu Arg Phe Arg Arg Ser Ala Asn Ser Leu Thr Leu Ile Asn Pro Thr Pro Tyr Tyr Leu Thr Val Thr Glu Leu Asn Ala Gly Thr Arg Val Leu Glu Asn Ala Leu Val Pro Pro Met Gly Glu Ser Ala Val Lys Leu Pro Ser Asp Ala Gly Ser Asn Ile Thr Tyr Arg Thr Ile Asn Asp Tyr Gly Ala Leu Thr Pro Lys Met Thr Gly Val Met Glu

For producing the transgenic cell line, the FimC gene from E. coli strain J96 was amplified with primers SLC4-28-fimC5 and SLC4-28-FimC3 from purified J96 genomic DNA to give a 771 base pair product. This was digested with BamHI and EcoRI, purified, and ligated into pTRC99a cut with the same enzymes (BamHI and EcoRI). The ligation product was transformed into E. coli C600 cells, and selected on ampicillin, producing plasmid pSJH-32.

The ampicillin antibiotic resistance was switched to kanamycin using the following procedure: Primers pKD4-pr1 and pKD4-pr2 were used to amplify the kanamycin resistance gene from pKD4. This PCR product was phosphorylated with T4 polynucleotide kinase and gel purified. pSJH-32 was cut with ScaI and BgII, blunted with T4 DNA polymerase, dephosphorylated with calf intestinal alkaline phosphatase, then ligated with the phosphorylated kanamycin resistance gene PCR product. The ligation product was then transformed into E. coli C600 cells and selected on kanamycin, creating plasmid pSJH-319.

The FimH gene from strain J96 was amplified with primers FimH5 and FimH3 from purified J96 genomic DNA to give a 978 base pair product. It was digested with SacI and HindIII, purified, and ligated into pBAD33 digested with SacI and HindIII. Afterwards the construct was transformed into C600 cells, and selected on chloramphenicol.

Example 3

Bioprocessing

Process to Obtain Antigens of the Vaccine

The bioprocessing step is initiated with inoculation of master cell bank (MCB) into shake flasks containing APS LB medium with kanamycin (50 μg/mL) and chloramphenicol (20 μg/mL). When the OD reaches 2.0-3.0 units (after approximately 15 hours growth), the cell culture is transferred aseptically into reactors for fed-batch fermentation. The medium containing APS Super Broth, about 0.8% glycerol, and antibiotics is sterilized prior to inoculation. FimH protein expression is induced at OD 10 with IPTG. Five minutes after IPTG addition, FimC protein expression is induced with arabinose. Cells are harvested approximately one hour later. After harvesting, the cells are separated from the media components by continuous or batch centrifugation.

Protein Recovery

Recombinant FimCH is expressed in the E. coli periplasm. E. coli, as a gram negative bacteria, possess an inner and an outer lipid bilayer membrane. The space between the lipid bilayers is the periplasm. Immediately after centrifugation, FimCH is recovered from the cell using a periplasm preparation. The cells are reacted with recombinant lysozyme in the presence of sucrose, Tris, and EDTA at 2-8° C. The mixture is then centrifuged, and the resulting periplasmic protein solution is collected. The protein is then precipitated with ammonium sulfate, centrifuged, resuspended in 20 mM MES pH 5.9, and diafiltered via dialysis into 20 mM MES pH 5.9 using SpectraPor 2 Dialysis Membrane (Spectrum Labs 132680). When the solution conductivity decreases to approximately ≤1.5 mS/cm, the solution is collected and transferred to purification.

Protein Purification

Purification consists of three column chromatography steps (1.CEX, 2. HIC, 3. CEX), one buffer exchange step via diafiltration using SpectraPor 2 Dialysis Membrane (Spectrum Labs 132680) followed by filtration, and one final aseptic filtration step. The diafiltration step is used to exchange the protein into 20 mM MES buffer pH 5.9 so that it will bind the second CEX column.

The two CEX steps use Source 15S (GE Healthcare 17-1273-02) in an XK26 column. For both CEX columns the following conditions are used: Buffer A: 20 mM MES, pH 5.9; Buffer B: 20 mM MES/500 mM Sodium Chloride, pH 5.9; 8 ml/min for all steps except loading for XK26/10 column, pre-equilibrate the column with 5 CV of Buffer B, equilibrate the column with 4 CV of Buffer A, load Dialyzed FimCH sample at 5 ml/min for XK26/10 using a sample pump and specifically not via the chromatography pump, wash the column with 4 CV of Buffer A, and elute the column with a linear 5 CV gradient from 0-25% Buffer B with fraction collection.

For the HIC column used Butyl Sepharose 4FF (GE Healthcare 17-0980-01) in XK26 column. Buffer C: 20 mM MES/550 mM Ammonium Sulfate, pH 5.9; 8 ml/min for XK26/10 except loading, pre-equilibrate the column with 3 CV of Buffer A (as above), equilibrate the column with 6 CV of Buffer C, load Pooled FimCH sample at 5 ml/min XK26/10 column, wash the column with 6 CV of Buffer C elute the column with a linear 4 CV gradient from 0-100% Buffer A with fraction collection. FimCH is formulated in the concentration of 0.3 mg/mL in 20 mM MES pH 5.9 or 20 mM trisodium citrate, pH 5.4. It is then aseptically filtered through a 0.2 μm sterile filter. FimCH is stable and can be stored at −20° C. for about at least 2 years.

Example 4

Potency by In Vitro Mannose Binding

Demonstrates the Biological Activity of FimCH

The biological activity of the FimCH drug substance (for example, from Example 3) is determined by an in vitro mannose binding assay. The FimH protein is a bacterial adhesin utilized by *E. coli* to bind mannose residues on glycosylated proteins. During urinary tract infections, the FimH adhesin binds mannosylated uroplakin proteins on bladder epithelial cells, which promotes the internalization of bound *E. coli*. The binding of FimH to mannosylated uroplakin is essential for *E. coli* to cause urinary tract infections. To monitor the mannose-binding activity of FimH in vitro, FimH binding to the enzyme horseradish peroxidase (HRP) is observed. HRP is a glycosylated protein containing mannose residues, and has previously been used to study mammalian mannose-binding receptors. Complexes of HRP and the lectin ConA, which binds α-D-mannosyl and α-D-glucosyl groups, have also been generated and studied. These results demonstrate that HRP acts as a ligand for other known mannose-binding proteins. Using this potency assay as described below, HRP binding to FimH is shown to be concentration-dependent and to be inhibited by small molecules that the block the binding of mannose to FimH.

Figure 3:
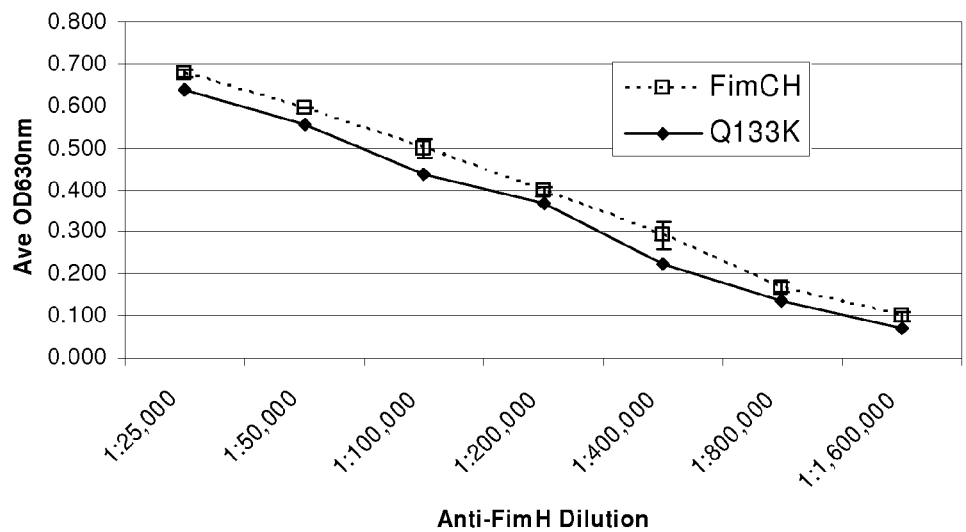
FIG. 3 is a graph illustrating the indirect ELISA of FimCH and Q133K using IgG anti-FimH.
Figure 4:
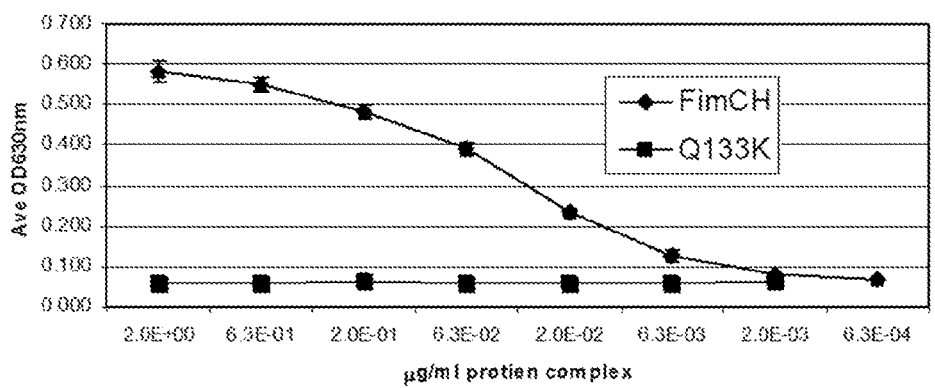
FIG. 4 is a graph illustrating the potency assay analyzing FimCH and Q133K.

In the in vitro FimCH potency assay, FimCH is "captured" by purified and qualified anti-FimH antisera bound to an ELISA plate. The anti-FimH antisera used in this assay have demonstrated the ability to bind to FimH in both indirect ELISAs (as the detection antisera, FIG. 3) and western blots. HRP is then added, excess HRP is rinsed away, and the activity of bound HRP is detected. The measured HRP activity is proportional to the concentration of FimCH added (FIG. 4). These results demonstrate that HRP binds to FimH in a dose-dependent manner.

To demonstrate that HRP binding to FimH requires FimH mannose-binding activity, a mannose binding-deficient FimH mutant named Q133K, which is also in complex with FimC, was analyzed and compared to FimCH. Q133K shares the same amino acid sequence as FimH, except that a critical glutamine at position 133 is replaced by lysine. This mutation is in the FimH mannose-binding pocket and renders Q133K functionally deficient in binding mannose and mannosylated proteins. As shown in FIG. 4, Q133K FimCH does not bind HRP. In an indirect ELISA (FIG. 3), the Q133K mutant complex is recognized by the purified anti-FimH antisera. This demonstrates that the lack of HRP signal with Q133K is not due to an inability of the purified antisera to bind to Q133K; instead, it is due to the inability of Q133K to bind mannose residues on HRP. These results also demonstrate that HRP does not bind FimC, because Q133K is also in complex with FimC.

As demonstrated in Hung et al. 2002, single point mutations in FimH at positions 54, 133, 135, and 140 completely abolish mannose binding. As reported by Hung et al., " . . . even the slightest change in the mannose-binding pocket, in an atom that does not bind directly to mannose, significantly reduces binding," suggesting that mutations that could occur in vitro could severely limit or abolish FimH mannose binding activity. The lack of HRP binding to the Q133K mutant supports this assay's ability to assess the biological activity of FimH binding to mannosylated proteins.

Figure 5:
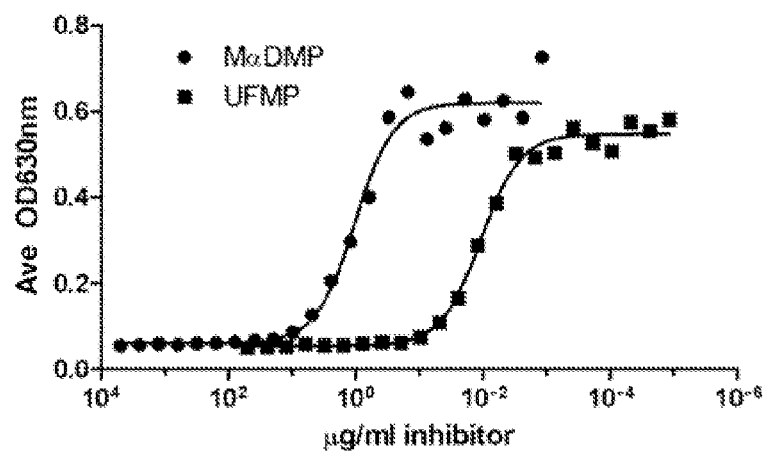
FIG. 5 is a graph illustrating the evaluation of small molecule inhibitors in the potency assay. Two small molecules, 4-methylumbelliferyl-α-D-mannopyranoside (UFMP) and methyl-α-D-mannopyranoside (MDMP) inhibit mannose binding to FimH.

Several small molecule inhibitors of mannose binding to FimH have been described. Two of these inhibitors, 4-methylumbelliferyl-α-D-mannopyranoside (UFMP) and methyl-α-D-mannopyranoside (MDMP), have been used to further qualify this potency assay. The reported dissociation constant (Kd) for UFMP binding to FimH is 20 nM, which is approximately 100-fold more potent than MDMP's Kd of 2.2 μM. As expected, the addition of either of these FimH mannose binding inhibitors in the HRP binding step blocks HRP binding to FimH in a dose-dependent manner (see FIG. 5). For UFMP, 50% inhibition is observed at 10 ng/mL (30 nM). For MDMP, 50% inhibition is observed at approximately 1 μg/mL (5.1 μM), which is approximately 100-fold higher than the concentration of UFMP.

These results demonstrate this assay's ability to assess the biological activity of FimH and verify the consistency of the manufacturing process from batch to batch. Furthermore, this potency assay confirms the proper folding of the FimH epitope and is predictive of the generation of IgG anti-FimH that has been shown to reduce *E. coli* CFU in bladders of mice by the administration of the FimCH/phosphorylated hexaacyl disaccharide vaccine.

Example 5

Impurities of FimCH Drug Substance by CEX-HPLC

Figure 6:
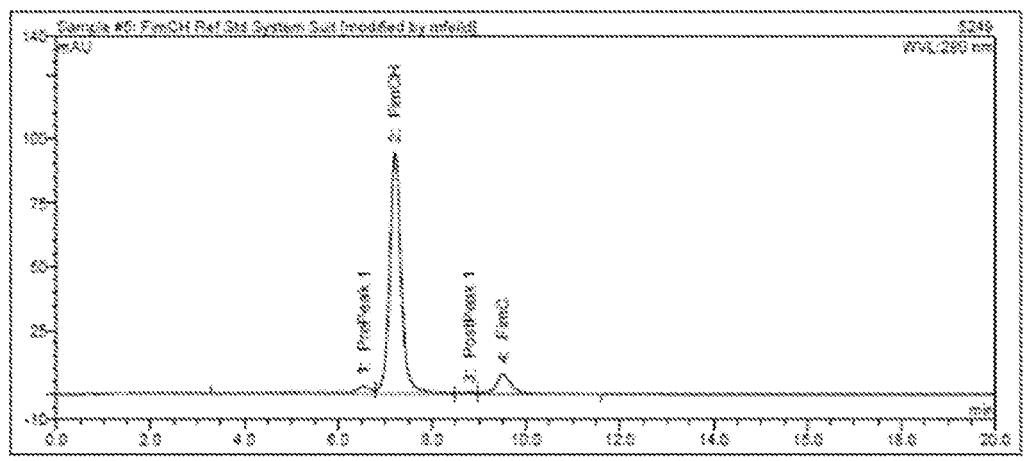
FIG. 6 is a representative chromatogram of the FimCH drug substance sample by CEX-HPLC.

CEX-HPLC is used for determination of the FimCH complex, unbound FimC and impurities in the final FimCH drug substance. The protein is eluted from a GE Healthcare Mono S 5/50 GL column using a gradient of 0.3 M NaCl in 20 mM MES buffer, pH 6.2 (Buffer B) (Buffer A is 20 mM MES buffer, pH 6.2). At T=0 the mobile phase is 100% Buffer A, and at T=22 minutes, the mobile phase is 100% Buffer B. The relative content of the unbound FimC and impurities is determined based on the peak areas. A representative chromatogram is provided in FIG. 6.

Example 6

FimCH and PHAD Formulation

An 85-Day Intramuscular Toxicity/Immunogenicity Study in Rabbits with a 21 Day Recovery Period (GLP)

The pivotal GLP toxicity study to evaluate the toxicity and immunogenicity of the FimCH vaccine containing a PHAD formulation of the invention (DPPC:PHAD—about 2.4:1 molar ratio) was conducted in female rabbits. The study examined ophthalmological findings, antibody assessment, and histopathology. Female rabbits were administered a total of 5 doses of saline control (N=6), PHAD alone at 40 to 50 µg (N=12), FimCH at 100 µg plus 20 µg PHAD (N=6; low dose), or FimCH at 125 µg plus 40 to 50 µg PHAD (N=12; high dose) via IM injection every 3 weeks (Days 1, 22, 43, 64, and 85) for 13 weeks. Three days following the fifth dose (Day 88), 6 rabbits per group were euthanized with the remaining 6 rabbits in the PHAD alone group and FimCH high dose groups euthanized following a 3-week recovery period (Day 106).

Toxicity was assessed based on clinical observation, ophthalmology, body temperature, body weight, food consumption, clinical pathology, gross necropsy, organ weight, and histopathology data. Body temperatures were obtained prior to and 2, 4, 6, 24, 48 and 72 hours after each injection. In addition to standard clinical pathology parameters (predose, Days 2 and 88), C-reactive protein (CRP) and fibrinogen were evaluated 2 and 7 days after dosing. Potential injection site reactions were scored for edema and erythema using the Draize scale and assessed for other manifestations of local toxicity (i.e. eschar, vesiculation, ulceration, and hematoma) 24, 48, and 72 hours post dose. Anti-FimH antibody assessment was performed on serum samples collected prior dosing on Days 1, 22, 43, 64 and 85, and prior to necropsy on Days 88 and 106, on urine samples collected prior to dosing, Day 64, and prior to necropsy on Days 88 and 106, and on vaginal washings collected prior dosing on Days 1 and, and prior to necropsy on Days 88 and 106. Antibody evaluation of the urine and vaginal wash samples was qualitative using a qualified MSD-ECL assay. Antibody levels in serum were determined using a validated MSD-ECL assay. Of 18 rabbits vaccinated with FimCH and PHAD, 17 demonstrated anti-FimH IgG titers at about 1:3,200,000 at about Day 88.

All rabbits survived to scheduled necropsy. Preliminary data indicated that FimCH plus PHAD as well as PHAD alone were well tolerated. The findings demonstrated that there were no apparent PHAD alone or vaccine-related effects on clinical observations, body weight, food consumption, body temperature, clinical pathology, or organ weights. Local reaction, based on in-life observations, was limited.

A similar rabbit study was performed using FimCH with PHAD prepared as DPPC:PHAD at about a molar ratio of 1:3.9. In this study, only 5 of 16 rabbits at about Day 43 demonstrated anti-FimH IgG titers from 1:400,000 to 1:800,000. In contrast, 16 of 18 rabbits vaccinated with FimCH with PHAD prepared as DPPC:PHAD at about a molar ratio of 2.4:1 (listed above) demonstrated anti-FimH IgG titers from 1:400,000 to 3,200,000 at about Day 43. These immunogenic differences are consistent with the studies performed in mice described herein demonstrating that a molar ratio of DPPC:PHAD of about 2.4:1 is superior to a molar ratio of DPPC:PHAD of about 1:3.9.

Example 7

Figure 7:
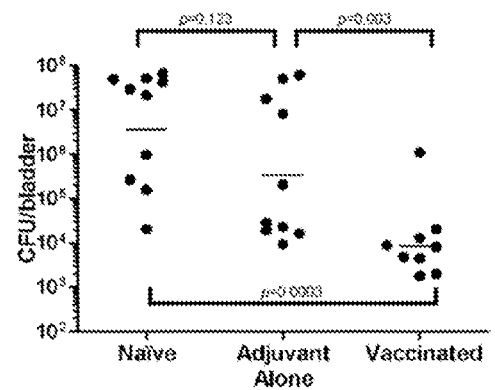
FIG. 7 is a graph illustrating the protection from *E. coli* Infection following FimCH/PHAD immunization of mice.

To test the efficacy of phosphorylated hexaacyl disaccharide as an adjuvant for systemic vaccination in the mouse UTI infection model, C3H/HeN mice were infected with approximately $1 \times 10^8$ CFU of clinical cystitis *E. coli* isolate UTI89 via transurethral catheterization after IM immunization. Female C3H/HeN mice (approximately 9 weeks old) were purchased from Charles River laboratories (Wilmington, Mass.). Mice were injected via the intramuscular route (IM) in the right thigh under light isoflurane anesthesia (Henry Schein, Melville, N.Y.) in a 50 µl volume using a 30 gauge needle. In these efficacy studies, mice were immunized with 12.5 µg PHAD/15 µg FimCH. Mice immunized using PHAD as the adjuvant and FimCH as antigen showed a statistically significant decrease of *E. coli* CFU in bladders one or two days after infection compared to mice immunized with adjuvant alone and to naïve mice (experiment using PHAD shown in FIG. 7). These data demonstrate that a FimCH vaccine adjuvanted with phosphorylated hexaacyl disaccharide produces antibodies in mice that reduce the *E. coli* colonization of bladders. These data offer evidence that a FimCH vaccine adjuvanted with phosphorylated hexaacyl disaccharide prepared according to the compositions described herein and used according to the methods described herein administered to a human patient in need will also reduce the *E. coli* colonization of bladders in humans.

Example 8

Truncated FimH (FimHt) Adjuvanted with phosphorylated hexaacyl disaccharide Formulation or Freund's Adjuvant An Immunogenicity Study in Rabbits Female rabbits were administered a total of 3 doses of FimHt at 100 µg plus about 50 µg PHAD formulation of the invention (N=2) on days 0, 21, and 42, or a total of 5 doses of FimHt at 100 µg plus Freund's adjuvant (complete for initial vaccination and incomplete for each boost at about days 14, 21, 49, and 70) (N=2) via IM injection. In this experiment, truncated FimH has a series of histidines or histidine tag, and those skilled in the art understand that other truncated versions of FimH can also be used, most preferably requiring the mannose binding domain. Truncated FimH in this example consists of FimH residues 1 to 175 with a C-terminal 6-histidine tag (SEQ ID No: 3). The sequence of FimH is described in Example 2. Anti-FimH antibody assessments were performed on serum samples collected on about day 30 or about days 35 and 56. Antibody levels in serum were determined using an ELISA as described herein. The capture antigen for this experiment was an equivalent truncated FimH without a histidine tag. Rabbits vaccinated with both formulations demonstrated anti-FimH IgG greater than 1:1,600,000 (preimmune sera<1:10,000). Previous truncated versions of FimH have been publicly disclosed and one example is as in U.S. Pat. No. 6,737,063, which is specifically incorporated in its entirety.

Example 9

FimCH Vaccine with phosphorylated hexaacyl disaccharide Formulation Administered to Rabbits Two groups of rabbits (N=3) were immunized at day 0 and boosted at days 21, 42, via IM injection with 50 µg FimCH and 54 µg PHAD with and without 0.1% polysorbate 80 (phosphorylated hexaacyl disaccharide formulation of the invention, 10 mM trisodium citrate, pH 6.0). Antibody levels in serum were determined using an ELISA as described herein. Serum was collected from both groups including at about day 30. IgG anti-FimH titers were approximately equivalent to or more than 1:1,600,000 in both groups (preimmune sera<1:10,000). The data described herein demonstrate that FimCH vaccine with phosphorylated hexaacyl disaccharide formulations of the invention with or without polysorbate 80 generate an equivalent immunogenic response.

Example 10

HPLC Analysis of PHAD and DPPC in Compositions

Figure 8:
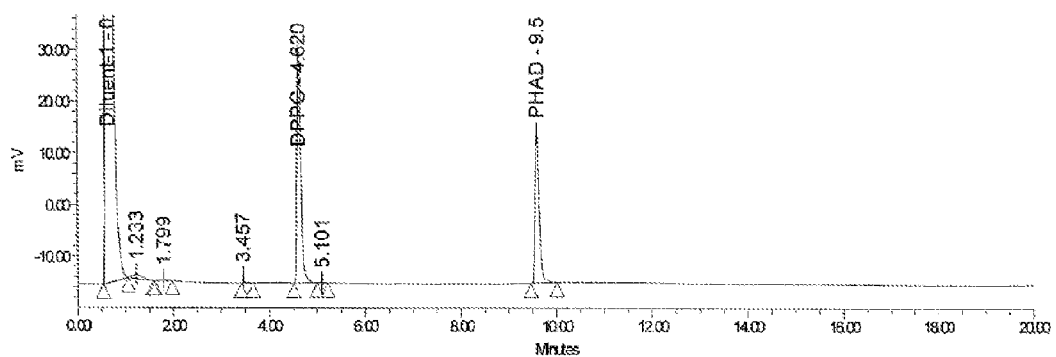
FIG. 8 is an example chromatogram of DPPC and PHAD by HPLC.

PHAD and DPPC concentrations in the PHAD formulation are analyzed by HPLC-ELSD using an Agilent Eclipse XBD C18, 1.8 um, 4.6 mm×50 mm column. The mobile phases are as follows: MP A: 20 mM ammonium acetate/1% acetic acid in water; MP B: 20 mM ammonium acetate/1% acetic acid in methanol; and MP C: 20 mM ammonium acetate/1% acetic acid in methanol/chloroform (50/50). Method 1: gradient begins at 5% MP A and 95% MP B, at 2 minutes is 100% MP B, and at 8 minutes is 100% MP C. Method 2: gradient begins at 5% MP A and 95% MP B, at 2 minutes is 100% MP B, and at 15 minutes is 100% MP C. Sample Diluent 1:85:15 (75:15:10 methanol:chloroform:water with 20 mM ammonium acetate/1% acetic acid):(1:1 methanol:chloroform with 20 mM ammonium acetate/1% acetic acid) Sample and standards are diluted 1:4 with sample diluent 1. Sample Diluent 2: (70:25:5) methanol:chloroform:water with 20 mM ammonium acetate/1% acetic acid. If using sample diluent 2, sample and standards are diluted 1:10 with sample diluent 2. The ELSD gain is at 8 with temperature at 60 C and nitrogen flow set to approximately 3.7 bars. An example chromatogram using method 2 and sample diluent 2 is shown in FIG. 8.

Example 11

Stability Studies of PHAD Compositions and Formulations

Using the HPLC method as described in Example 10, the stabilities of different preparations of PHAD as a suspension or PHAD formulations as a suspension including phosphatidylcholines were monitored by analyzing these preparations for PHAD concentration and comparing it to its initial results. A PASS result means the PHAD concentration was within plus/minus 20% of the initial testing results of the release samples, which is within the limits of the HPLC method using an evaporative light scattering detector (ELSD). PHAD concentrations of these preparations were compared when stored at 2° C. to 8° C. or 25° C. or to 37° C. to project (estimate) the stability of these preparation over months to years. To those skilled in the art, data from 25° C. is an intermediate/accelerated condition and data from 37° C. is an accelerated condition used to project a shelf life at the long term storage condition of 2° C. to 8° C. Buffers that enabled superior stability for PHAD were first determined; then these preferred buffers were evaluated with a PHAD formulation including a phophatidylcholine.

TABLE 3

Stability of PHAD at 25° C. for 7 days in Select Buffers

| | Condition/Time Point | Result |
|---|---|---|
| 1 0.5 mg/ml PHAD in WATER | 25° C./7 days | FAIL |
| 2 0.5 mg/ml PHAD in 10 mM trisodium citrate, pH 6.0 | 25° C./7 days | PASS |
| 3 0.5 mg/ml PHAD in 10 mM trisodium citrate, pH 5.0 | 25° C./7 days | PASS |

TABLE 3-continued

Stability of PHAD at 25° C. for 7 days in Select Buffers

| | Condition/Time Point | Result |
|---|---|---|
| 4 0.5 mg/ml PHAD in 50 mM trisodium citrate, pH 6.0 | 25° C./7 days | PASS |
| 5 0.5 mg/ml PHAD in 100 mM trisodium citrate, pH 6.0 | 25° C./7 days | FAIL |
| 6 0.5 mg/ml PHAD in 10 mM sodium acetate, pH 6.0 | 25° C./7 days | FAIL |
| 7 0.5 mg/ml PHAD in 10 mM disodium succinate, pH 6.0 | 25° C./7 days | PASS |
| 8 0.5 mg/ml PHAD in Phosphate buffered saline (PBS) | 25° C./7 days | FAIL |
| 9 0.5 mg/ml PHAD in 200 mM $Na_2HPO_4$ and 100 mM citric acid, pH 6.0 | Not applicable | precipitate |
| 10 0.5 mg/ml PHAD in 20 mM $Na_2HPO_4$ and 10 mM citric acid, pH 6.0 | 25° C./7 days | PASS |
| 11 0.5 mg/ml PHAD in 10 mM $Na_2HPO_4$, pH 6.0 | 25° C./7 days | PASS |

The data in the table above demonstrate that citrate, succinate, and phosphate buffers from about 10 mM to 50 mM are superior to certain others buffers examined, and provide stability at the listed temperatures for the listed time periods.

TABLE 4

Stability of PHAD at 25° C. for 30 or 60 days and 37° C. for 7, 60 days, or 4 months in Select Buffers

| | Condition/Time Point | Result |
|---|---|---|
| 0.5 mg/ml PHAD in 20 mM $Na_2HPO_4$ and 10 mM citric acid, pH 6.0 | 25° C./30 days | FAIL |
| 0.5 mg/ml PHAD in Phosphate buffered saline (PBS) | 25° C./30 days | FAIL |
| 0.5 mg/ml PHAD in 10 mM trisodium citrate, pH 5.0 | 25° C./30 days | PASS |
| 0.5 mg/ml PHAD in 10 mM trisodium citrate, pH 6.0 | 25° C./30 days | FAIL |
| 0.5 mg/ml PHAD in 10 mM $Na_2HPO_4$, pH 6.0 | 25° C./60 days | FAIL |
| 0.5 mg/ml PHAD in 10 mM disodium succinate, pH 6.0 | 25° C./60 days | FAIL |
| 0.5 mg/ml PHAD in 50 mM trisodium citrate, pH 6.0 | 25° C./60 days | PASS |
| 0.5 mg/ml PHAD in 10 mM trisodium citrate, pH 6.0 | 37° C./7 days | PASS |
| 0.5 mg/ml PHAD in 30 mM trisodium citrate, pH 6.0 | 37° C./7 days | PASS |
| 0.5 mg/ml PHAD in 50 mM trisodium citrate, pH 6.0 | 37° C./7 days | PASS |
| 0.5 mg/ml PHAD in 10 mM $Na_2HPO_4$, pH 6.0 | 37° C./7 days | PASS |
| 0.5 mg/ml PHAD in 50 mM $Na_2HPO_4$, pH 6.0 | 37° C./7 days | PASS |
| 0.5 mg/ml PHAD in 10 mM trisodium citrate, 10 mM $Na_2HPO_4$, pH 6.0 | 37° C./7 days | PASS |
| 0.5 mg/ml PHAD in 10 mM trisodium citrate, pH 6.0 | 37° C./60 days | FAIL |
| 0.5 mg/ml PHAD in 30 mM trisodium citrate, pH 6.0 | 37° C./60 days | PASS |
| 0.5 mg/ml PHAD in 50 mM trisodium citrate, pH 6.0 | 37° C./60 days | PASS |
| 0.5 mg/ml PHAD in 50 mM $Na_2HPO_4$, pH 6.0 | 37° C./60 days | PASS |
| 0.5 mg/ml PHAD in 10 mM trisodium citrate, 10 mM $Na_2HPO_4$, pH 6.0 | 37° C./60 days | FAIL |
| 0.5 mg/ml PHAD in 10 mM trisodium citrate, pH 6.0 | 37° C./4 months | FAIL |
| 0.5 mg/ml PHAD in 30 mM trisodium citrate, pH 6.0 | 37° C./4 months | PASS |
| 0.5 mg/ml PHAD in 50 mM trisodium citrate, pH 6.0 | 37° C./4 months | PASS |
| 0.5 mg/ml PHAD in 50 mM $Na_2HPO_4$, pH 6.0 | 37° C./4 months | PASS |

The data in the table 4 demonstrate that citrate and phosphate buffers from about 30 mM to about 50 mM are superior to the other buffers examined. The citrate and phosphate buffers provide stability at the listed temperatures for the listed time periods. The data demonstrate the remarkable benefit of stability of increasing the citrate and phosphate concentrations to about 25 mM to about 50 mM, more preferably 28 mM to about 50 mM, and most preferably 30 mM to about 50 mM. The preferred use of succinate as a buffer is shown from all of the data collectively as described herein. Stability of phosphorylated hexaacyl disaccharide at 37° C. for 60 or more days in 30 mM to 50 mM citrate and phosphate buffers is unknown in the prior art and is an important aspect of the invention.

TABLE 5

Stability of a 0.5 mg/ml PHAD Formulation of the Invention in Select Buffers and Select Phosphatidylcholines at 25° C. for 60 days without Polysorbate 80 and without Extrusion. The phosphatidylcholines were prepared at about a molar ratio of 2.5 to 1 to PHAD.

| | Condition/Time Point | Result |
|---|---|---|
| PHAD formulation with DPPC in 10 mM trisodium citrate, pH 6.0 | 25° C./60 days | PASS |
| PHAD formulation with POPC in 10 mM trisodium citrate, pH 6.0 | 25° C./60 days | PASS |
| PHAD formulation with DMPC in 10 mM trisodium citrate, pH 6.0 | 25° C./60 days | PASS |
| PHAD formulation with DPPC in 50 mM trisodium citrate, pH 6.0 | 25° C./60 days | PASS |
| PHAD formulation with DPPC in 10 mM disodium succinate, pH 6.0 | 25° C./60 days | PASS |
| PHAD formulation with POPC in 10 mM disodium succinate, pH 6.0 | 25° C./60 days | PASS |
| PHAD formulation with DMPC in 10 mM disodium succinate, pH 6.0 | 25° C./60 days | PASS |
| PHAD formulation with DPPC in 10 mM $Na_2HPO_4$, pH 6.0 | 25° C./60 days | PASS |

The data in the Table 5 demonstrate the remarkable and unexpected benefit of combining the citrate, succinate, and phosphate buffers at about 10 mM to 50 mM with a phosphatidylcholine of the invention. The combination of the preferred buffers of the invention with a phosphatidylcholine results in superior stability of phosphorylated hexaacyl disaccharide in the formulation compared to buffer alone.

TABLE 6

| | | Condition/Time Point | Result |
|---|---|---|---|
| 1 | Adjuvant formulation of Example 1 except reconstituted in WATER, not extruded, and without polysorbate 80 | 25° C./14 days | FAIL |
| | | 2-8° C./1 month | PASS |
| | | 25° C./1 month | FAIL |
| | | 2-8° C./2 months | PASS |
| | | 25° C./2 months | FAIL |
| 2 | Adjuvant formulation of Example 1 (in trisodium citrate, pH 6.0 as stated above) not extruded and without polysorbate 80 | 25° C./7 days | PASS |
| | | 25° C./8 days | PASS |
| | | 25° C./1 month | PASS |
| | | 25° C./2 months | PASS |
| 3 | Adjuvant Formulation of Example 1 (Lot 1214P69) | 2-8° C./8 months | PASS |
| | | 25° C./8 months | PASS |
| 4 | Adjuvant Formulation of Example 1 (Lot ENG-1) | 2-8° C./3 months | PASS |
| | | 25° C./2 months | PASS |
| | | 2-8° C./5 months | PASS |
| | | 25° C./4 months | PASS |
| 5 | Adjuvant Formulation of Example 1 | 2-8° C./3 months | PASS |
| | | 25° C./3 months | PASS |
| | | 2-8° C./6 months | PASS |
| | | 25° C./6 months | PASS |
| 6 | FimCH Vaccine, 17 mM trisodium citrate, pH 5.4, consisting of: 0.1 mg/ml adjuvant formulation of Example 1 without polysorbate 80 0.2 mg/ml FimCH, pH 5.4 | 2-8° C./4 days | PASS |
| | | 25° C./4 days | PASS |
| | | 2-8° C./3 months | PASS |
| | | 2-8° C./4 months | PASS |

As shown in Table 6, it is the combination of citrate at about 10 mM with specific molar ratios of DPPC to phosphorylated hexaacyl disaccharide provides long-term stability at about 25° C.

As shown in the tables above, formulations prepared in water are stable short-term when stored at 2° C. to 8° C.; however, the long sought-after goal is to reduce cold chain storage and management. The inventive adjuvant formulation disclosed herein achieved this goal by providing an adjuvant formulation with extended stability at room temperature to about 37° C. The data in Table 6 clearly show that the PHAD concentration of these formulations prepared in citrate buffer will remain stable for at least approximately 6 or more months at about 25° C. and potentially 2 to 3 years at 2° C. to 8° C.

The addition of citrate, succinate, or phosphate buffer to the Phosphatidylcholine:phosphorylated hexaacyl disaccharide formulations remarkably and unexpectedly enables storage at room temperature and exposure up to and at about 37° C. Phosphatidylcholine:phosphorylated hexaacyl disaccharide formulations prepared in water can produce equivalent immunogenic responses in mice and rabbits but are not stable at about 25° C.

Example 12

Particle sizes and zeta potentials were determined on PHAD formulations using Dynamic Light Scattering with the Malvern Zetasizer® ZS90 or Brookhaven Instruments Corp. using ZetaPlus Particle Sizing software. The manufacturer's directions and recommendations were followed. Table 7 provides representative data. Zeta potential values are used as one piece of qualitative data estimating the electrical charge at a bilayer and as described herein. Stability of the PHAD formulations is experimentally determined from particle size of the formulation and concentration of PHAD.

TABLE 7

| | Sample | Mean Effective Diameter (nm) | Zeta Potential (mV) |
|---|---|---|---|
| 1 | Adjuvant formulation of Example 1, not extruded and without polysorbate 80 | 207 | −56 |
| 2 | Adjuvant formulation of Example 1, containing DPPC:PHAD at a molar ratio of about 13:1, not extruded and without polysorbate 80 | 309 | −37 |
| 3 | Adjuvant formulation of Example 1, containing DMPC and not DPPC, not extruded and without polysorbate 80 | 293 | −72 |
| 4 | Adjuvant formulation of Example 1, containing DMPC:DLPC and not DPPC, in an approximate molar ratio with PHAD at 1.2:1.2:1 (DMPC:DLPC:PHAD) not extruded and without polysorbate 80 | 202 | −76 |
| 5 | Adjuvant formulation of Example 1 without polysorbate 80 | 79 | −46 |
| 6 | Adjuvant formulation of Example 1 | 71 | −40 |
| 7 | Adjuvant formulation of Example 1, extruded at room temperature and without polysorbate 80 | 185 | −73 |
| 8 | DPPC alone (no PHAD) as prepared in Example 1 without extrusion and without polysorbate 80 | 1393 | −6 |

As shown above, DPPC alone has a significantly less zeta potential and much larger mean particle size compared to the formulations of the invention containing PHAD. The critical micelle concentration of DPPC is about 0.46 nanomolar. These data offer evidence that DPPC alone is a significantly different composition than a DPPC and PHAD composition.

Example 13

The particle sizes of PHAD formulations of Example 1 prepared with or without polysorbate 80 or glycerol were compared when stored at 2° C. to 8° C. or about 25° C. to project (estimate) the stability of the particle sizes of the PHAD formulations over 12 to 36 months. Multiple batches of PHAD formulations were prepared and typically exhibited particles sizes between 70 to 100 nm immediately after extrusion. The goal for these PHAD formulations is to ensure that their mean effective diameter remains preferably less than 150 nm over its shelflife, even more preferably less than 130 nm, which is predicted to be 2 to 3 years or longer based upon the data described herein. It is important to trend the mean effective diameter over a certain time period at intermediate/accelerated conditions, e.g. 25° C., to assist with predicting the particle size at 2° C. to 8° C. in approximately 2 or more years.

Particle sizes and zeta potentials were determined using Dynamic Light Scattering with the Malvern Zetasizer® ZS90 or Brookhaven Instruments Corp. using ZetaPlus Particle Sizing software. The instrument manufacturer's directions and recommendations were followed.

TABLE 8

| Sample | Time Point/ Condition | Mean Effective Diameter (nm) |
|---|---|---|
| Adjuvant formulation of Example 1 without polysorbate 80 | 1 month/25° C. | 99 |
| Adjuvant formulation of Example 1 with 0.1% polysorbate 80 | 1 month/25° C. | 104 |
| Adjuvant formulation of Example 1 | 1 month/2-8° C. | 79 |
| Adjuvant formulation of Example 1 | 1 month/25° C. | 82 |
| Adjuvant formulation of Example 1 with 0.01% polysorbate 80 | 1 month/25° C. | 105 |
| Adjuvant formulation of Example 1 without polysorbate 80 | 4 months/2-8° C. | 83 |
| Adjuvant formulation of Example 1 without polysorbate 80 | 4 months/25° C. | 114 |
| Adjuvant formulation of Example 1 with 0.1% polysorbate 80 | 4 months/2-8° C. | 94 |
| Adjuvant formulation of Example 1 with 0.1% polysorbate 80 | 4 months/25° C. | 106 |
| Adjuvant formulation of Example 1 with 0.01% polysorbate 80 | 4 months/2-8° C. | 90 |
| Adjuvant formulation of Example 1 with 0.01% polysorbate 80 | 4 months/25° C. | 114 |
| Adjuvant formulation of Example 1 | 4 months/25° C. | 86 |
| Adjuvant formulation of Example 1 | 5 months/2-8° C. | 82 |
| Adjuvant formulation of Example 1 | 6 months/25° C. | 101 |
| Adjuvant formulation of Example 1 | 6 months/2-8° C. | 94 |
| Adjuvant formulation of Example 1 without polysorbate 80 | 8 months/2-8° C. | 117 |

The data presented in Table 8 in this example project that the particle sizes of the PHAD formulations stored at 2° C. to 8° C. without polysorbate 80 will remain below 150 nm for approximately a minimum of 2 years, and suggest potentially 3 years as described below. In this specific example and only for the purpose of this test, stable means that the mean effective diameter remains below 150 nm within the limitations of the instrument. To those skilled in the art, data from 25° C. is an intermediate/accelerated condition used to project a shelf life at the long term storage condition of 2° C. to 8° C. These data clearly project that the particle sizes of these PHAD formulations will remain stable for at least 6 or more months at about 25° C. and potentially 3 years at 2° C. to 8° C. As described herein, this stability of these PHAD formulations at 25° C. is unknown in the prior art and unexpected.

Example 14

A Comparison of the Formulations of the Invention to Other Adjuvant Formulations at Inducing Anti-FimH Antibodies in Mice The PHAD formulation of the invention or aqueous formulation (Aqueous formulation in this example refers to the molar ratio of lipid to adjuvant described in U.S. Pat. No. 6,491,919 and US Patent Application 20080131466) used below in this example were prepared as described in Example 1 with the following exceptions. The specified lipid(s) and/or molar ratios (shown in parentheses) were used and sonication occurred at about 45° C. for about 30 minutes to 2 hours as needed to achieve a homogenous suspension. All lipids were purchased from Avanti Polar Lipids as previously described herein.

Female C3H/HeN mice (approximately 9 weeks old) were purchased from Charles River laboratories (Wilmington, Mass.). Mice were injected via the intramuscular route (IM) in the right thigh under light isoflurane anesthesia (Henry Schein, Melville, N.Y.) in a 50 μl volume using a 30 gauge needle. Mice were vaccinated with 12.5 μg PHAD or Freund's adjuvant C (subcutaneous administration), and 15 μg FimCH, on days 1 and 29. As known to those skilled in the art, when used, complete Freund's adjuvant was given on day 1 and incomplete Freund's adjuvant on day 29.

ELISA for serum antibody detection: Sera was collected from the mice at sacrifice and analyzed by ELISA for anti-FimH antibodies. FimH truncate T3 was adhered to Immulon 4 HBX plates (ThermoFisher) at 2 μg/ml in PBS overnight at 4° C. After washing with PBS+0.05% TWEEN 20 (polyethylene glycol sorbitan monolaurate), open binding sites were blocked with 1.5% BSA (Sigma Aldrich) in PBS for 1 hr. After washing, dilutions of sample sera (in PBS with 0.05% TWEEN 20 (polyethylene glycol sorbitan monolaurate), 0.1% BSA, 0.5% methyl α-D-mannopyranoside) were incubated for 2 hrs. After washing, 1:500 diluted biotinylated Goat anti-Mouse IgG detection antisera (Sigma Aldrich) in sample dilution buffer was incubated in the wells overnight at 4° C. After washing, 1:25,000 diluted Avidin-Horse Radish Peroxidase (HRP, Sigma Aldrich) in sample dilution buffer was incubated in the wells for 20 minutes. After washing, HRP activity was detected using TMB substrate in Phosphocitrate buffer (Sigma Aldrich). Optical density was read at 630 nm using a VERSAMAX PLUS microplate reader and analyzed using SOFTMAX Pro analysis software (Molecular Devices, Sunnyvale, Calif.). Antibody titer was defined as the highest dilution with signal above background.

TABLE 9

| Adjuvant/Formulation | Antibody Dilution Titers |
|---|---|
| No Adjuvant; N = 6 mice | 1:20,000 |
| Experiment 1: Reference Adjuvant:Freund's adjuvant; N = 6 mice | 1:200,000 |
| Experiment 2: Reference Adjuvant:Freund's adjuvant; N = 7 mice | 1:200,000 |
| Experiment 1: DPPC:PHAD (1:3.9) aqueous formulation; N = 8 mice | 1:200,000 |
| Experiment 2: DPPC:PHAD (1:3.9) aqueous formulation; N = 10 mice | 1:200,000 |
| DPPC:PHAD (2.6:1) adjuvant formulation; N = 10 mice | 1:400,000 |
| DPPC:PHAD (13:1) adjuvant formulation; N = 10 mice | 1:400,000 |
| DPPC:DPPG:PHAD (2.6:0.3:1) adjuvant formulation; N = 10 mice | 1:400,000 |
| DPPC:DPPG:PHAD (2.6:2.6:1) adjuvant formulation; N = 10 mice | 1:400,000 |

As clearly shown in Table 9, a molar ratio of DPPC to PHAD of about 2:1 to about 13:1 was superior at enhancing an immune response to FimH in mice when compared to no adjuvant, Freund's adjuvant, or the aqueous formulation of DPPC to PHAD at a molar ratio of 1:3.9. Freund's adjuvant is considered a standard adjuvant used in animal experiments.

The data shows that the molar ratio of the invention described herein of about 2:1 to 13:1 is superior to this frequently used preclinical adjuvant. This is one aspect of the invention that demonstrates its superiority to the prior art formulations. The data in Table 9 also demonstrate that adding DPPG into these formulations does not diminish the intended use of the PHAD formulations, i.e., to enhance an immune response to FimH.

Example 15

Determination that the Formulations of the Invention remain a Homogenous Mixture within 24 Hours. The procedure of Example 1 was used to prepare the PHAD formulation with a molar ratio of DPPC:PHAD at about 2.5 to 1, except polysorbate 80 was not added. The vial containing the PHAD formulation was gently inverted about three to five times. Then, the PHAD formulation was allowed to remain at room temperature for about 24 hours. After 24 hours and without inverting, shaking, or stirring the PHAD formulation, small aliquots were carefully removed from the top, middle, and bottom of the PHAD suspension. These aliquots were analyzed for PHAD concentration via HPLC as previously described herein. The results demonstrated that the aliquots from the top, middle, and bottom contained equivalent PHAD concentrations. These results demonstrate the PHAD formulation of the invention does not settle within 24 hours.

Example 16

Formulations of the Invention Used in Human Clinical Study

The adjuvant formulation of Example 1 and FimCH were prepared under cGMP for use in a human clinical study involving females of about 21 to 64 years of age. A vaccine of FimCH and PHAD formulation was prepared by adding a predetermined volume of a PHAD formulation to a vial of FimCH as previously described herein to obtain the preferred concentrations of FimCH and PHAD per each vial. An appropriate volume of the prepared vaccine was injected IM (intramuscular) to administer either 50 μg or about 107 μg of FimCH with either 10 μg, 20 μg, or about 40 μg of PHAD to each female subject.

From these IM injections in humans, the vaccine demonstrates that the adjuvant formulation of the invention with FimCH produces less severe injection site and systemic reactions in humans compared to certain other known adjuvant formulations used in humans. This is a remarkable aspect of the invention. Interim Data from Injection Site and Systemic Reactions are shown below for number of injections as of the interim analysis per female. The human study is ongoing and the females in the study are scheduled to receive 4 injections.

TABLE 10

| | Number of Females | FimCH/ PHAD dose in micrograms | Number of Injections | Severe Injection Site and Systemic Reactions |
|---|---|---|---|---|
| Group 1 | 5 | 107 μg/0 μg | 3 to 4 | None |
| Group 2 | 8 | 50 μg/10 μg | 2 to 3 | None |
| Group 3 | 16 | 50 μg/20 μg | 1 to 2 | None |
| Group 4 | 8 | 50 μg/40 μg | 1 | None |

At the time of this interim analysis, more than 60 IM injections to 37 females had been made and no severe injection site and systemic reactions have been observed. At the time of this interim analysis, females in Group 2 have demonstrated an antibody response to FimH after two IM injections greater than 10-fold from initial values prior to vaccination. These data demonstrate the vaccine is producing the intended antibody response against FimH. Females in this study will receive up to 4 IM injections of the vaccine. Groups 5 and 6 will open enrollment for females with a history of recurrent UTI.

In comparison, administration of the Cervarix vaccine that contains the adjuvants MPL with alum results in approximately 8% to more than 10% of subjects exhibiting severe injection site reactions and systemic reactions. As reported in the publication of Treanor et al. (Vaccine, 2013, 31(48), 5760-5), PHAD has been prepared in different formulations with squalene and administered to humans. Per this report, 5 μg of PHAD in this formulation resulted in severe local reactions, chills, and rigor and was so limiting that use of this formulation in future studies only contained 2 or less micrograms of PHAD. At 1 micrograms of PHAD in this formulation, severe injection site reactions and systemic reactions were still observed. In this formulation of Treanor et al. at 2 or less micrograms of PHAD, the benefits of the adjuvant PHAD producing an immune response are limited thereby robbing the potential of PHAD due to an inferior formulation. However, the adjuvant formulation of the invention overcomes this limitation with superior formulations that enable administration of up to 50 μg of phosphorylated hexaacyl disaccharide, or potentially more, with less severe injection site and systemic reactions. These human data offer evidence that phosphorylated hexaacyl disaccharide can be administered to humans at 100 μg or more micrograms with the formulations described herein. The adjuvant formulations of the invention are superior to those formulations previously attempted.

All references, including without limitation all papers, publications, presentations, texts, reports, manuscripts, brochures, internet postings, journal articles, periodicals, and the like, cited in this specification are hereby incorporated by reference. The discussion of the references herein is intended merely to summarize the assertions made by their authors and no admission is made that any reference constitutes prior art. The inventors reserve the right to challenge the accuracy and pertinence of the cited references.

It is intended that all patentable subject matter disclosed herein be claimed and that no such patentable subject matter be dedicated to the public. Thus, it is intended that the claims be read broadly in light of that intent. In addition, unless it is otherwise clear to the contrary from the context, it is intended that all references to "a" and "an" and subsequent corresponding references to "the" referring back to the antecedent basis denoted by "a" or "an" are to be read broadly in the sense of "at least one." Similarly, unless it is otherwise clear to the contrary from the context, the word "or," when used with respect to alternative named elements is intended to be read broadly to mean, in the alternative, any one of the named elements, any subset of the named elements or all of the named elements.

In view of the above, it will be seen that the several advantages of the invention are achieved and other advantageous results obtained. It should be understood that the aforementioned embodiments are for exemplary purposes only and are merely illustrative of the many possible specific embodiments that can represent applications of the principles of the invention. Thus, as various changes could be made in the above methods and compositions without departing from the scope of the invention, it is intended that all matter contained in the above description as shown in the accompanying drawings shall be interpreted as illustrative and not in a limiting sense.

Moreover, one of ordinary skill in the art can make various changes and modifications to the invention to adapt it to various usages and conditions, including those not specifically laid out herein, without departing from the spirit and scope of this invention. Accordingly, those changes and modifications are properly, equitably, and intended to be, within the full range of equivalents of the invention disclosed and described herein.

The invention claimed is:

1. A method for administering a vaccine composition to a human comprising the steps of:

administering to the human a vaccine composition comprising an adjuvant formulation comprising about 20 μg to about 50 μg of phosphorylated hexaacyl disaccharide, a phosphatidylcholine, and a buffer selected from the group consisting of citrate and succinate from about 10 mM to about 50 mM, wherein the phosphatidylcholine is at a molar ratio with phosphorylated hexaacyl disaccharide at about 1:1 to about 20:1, and the vaccine composition is an aqueous buffered suspension.

2. The method of claim 1, wherein the phosphorylated hexaacyl disaccharide is present in an amount from about 40 μg to about 50 μg.

3. The method of claim 1, wherein the buffer is at a concentration of 15 mM to about 50 mM.

4. The method of claim 1, wherein the buffer is at a concentration of 20 mM to about 50 mM.

5. The method of claim 1, wherein phosphorylated hexaacyl disaccharide is comprised of

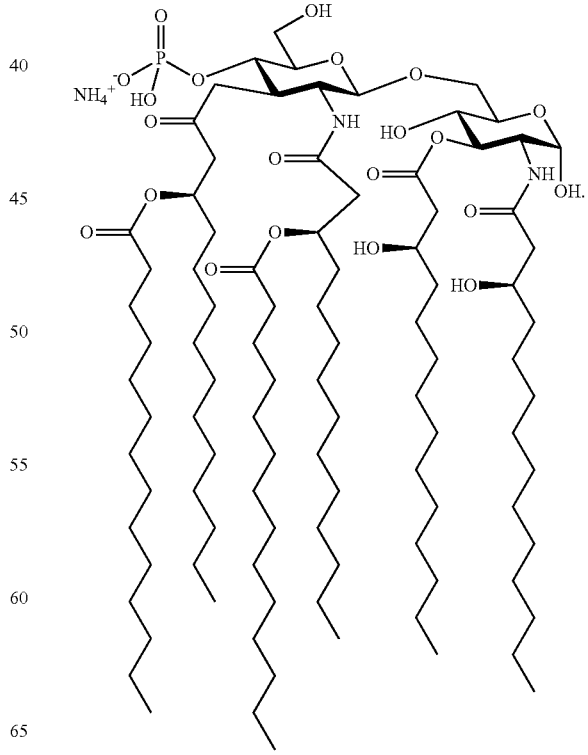

6. The method of claim 1, wherein the buffer is citrate.

7. The method of claim 1, wherein the buffer is succinate.

8. The method of claim 1, wherein the vaccine composition comprises an effective amount of FimCH or truncated FimH.

9. The method of claim 1, wherein the vaccine composition comprises an effective amount of FimCH.

10. The method of claim 1, wherein the vaccine composition is for the treatment of recurrent urinary tract infections.

11. The method of claim 1, wherein phosphatidylcholine is selected from the group consisting of 1,2-dimyristoyl-sn-glycero-3-phosphocholine (DMPC), 1,2-dipalmitoyl-sn-glycero-3-phosphocholine (DPPC), 1,2-distearoyl-sn-glycero-3-phosphocholine (DSPC), 1-palmitoyl-2-oleoyl-sn-glycero-3-phosphocholine (POPC), and 1,2-dioleoyl-sn-glycero-3-phosphocholine (DOPC).

12. The method of claim 1, wherein the phosphatidylcholine is selected from the group consisting of DMPC, DPPC, and DSPC.

13. The method of claim 1, wherein the phosphatidylcholine is at a molar ratio with phosphorylated hexaacyl disaccharide at about 2:1 to about 5:1.

14. The method of claim 11, wherein the phosphatidylcholine is at a molar ratio with phosphorylated hexaacyl disaccharide at about 2:1 to about 5:1.

15. The method of claim 12, wherein the phosphatidylcholine is at a molar ratio with phosphorylated hexaacyl disaccharide at about 2:1 to about 5:1.

16. The method of claim 1, wherein the vaccine composition has a mean particle size of 150 nanometers or less.

17. The method of claim 1, wherein the vaccine composition is essentially free of a second adjuvant.

18. The method of claim 1, wherein the vaccine composition is substantially free of saline.

19. The method of claim 18, wherein the phosphorylated hexaacyl disaccharide is comprised of

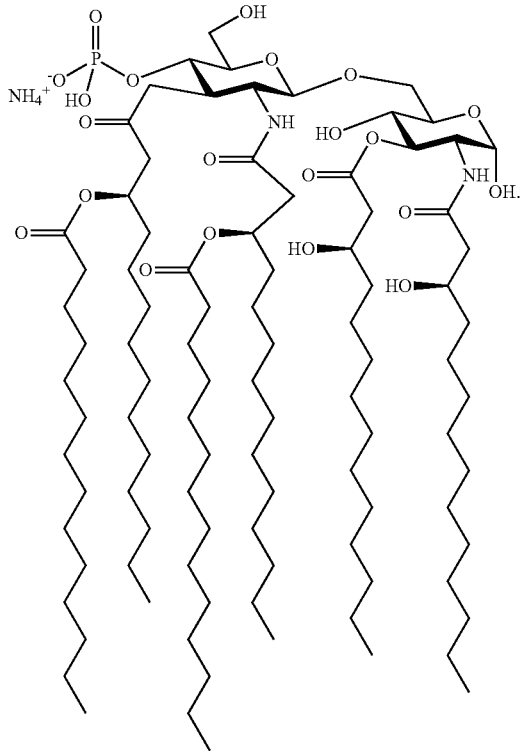

20. The method of claim 1, wherein the vaccine composition is substantially free of cholesterol.

21. The method of claim 1, wherein the vaccine composition is essentially free of cholesterol.

22. A method for administering a vaccine composition to a human comprising the steps of:
administering to the human a vaccine composition comprising an adjuvant formulation comprising about 20 µg to about 50 µg of phosphorylated hexaacyl disaccharide; phosphatidylcholine at a molar ratio with phosphorylated hexaacyl disaccharide at about 2:1 to about 5:1; phosphatidylcholine is selected from the group consisting of DMPC, DPPC, DSPC, POPC, and DOPC; and a buffer selected from the group consisting of citrate and succinate from 15 mM to about 50 mM, wherein the vaccine composition is an aqueous buffered suspension.

23. The method of claim 22, wherein the phosphorylated hexaacyl disaccharide is comprised of

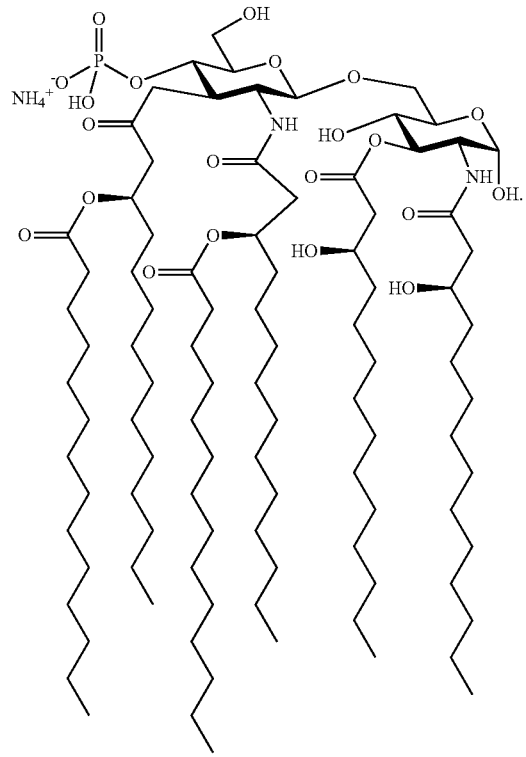

24. The method of claim 22, wherein the buffer concentration is from 25 mM to about 50 mM.

25. The method of claim 22, wherein the vaccine composition is essentially free of a second adjuvant.

26. The method of claim 22, wherein the vaccine composition comprises an effective amount of FimCH or truncated FimH.

27. The method of claim 22, wherein the vaccine composition comprises an effective amount of FimCH.

28. The method of claim 22, wherein the vaccine composition comprises about 40 µg to about 50 µg of phosphorylated hexaacyl disaccharide, the buffer is citrate, and an effective amount of FimCH, wherein the vaccine composition is essentially free of a second adjuvant.

29. An adjuvant formulation for a vaccine comprising:
phosphorylated hexaacyl disaccharide;
a phosphatidylcholine; and,
a buffer selected from the group consisting of citrate and succinate,
wherein the buffer concentration is from about 10 mM to about 50 mM, and the phosphatidylcholine is at a molar ratio with phosphorylated hexaacyl disaccharide at about 1:1 to about 20:1.

30. The adjuvant formulation of claim 29 wherein the phosphorylated hexaacyl disaccharide is comprised of
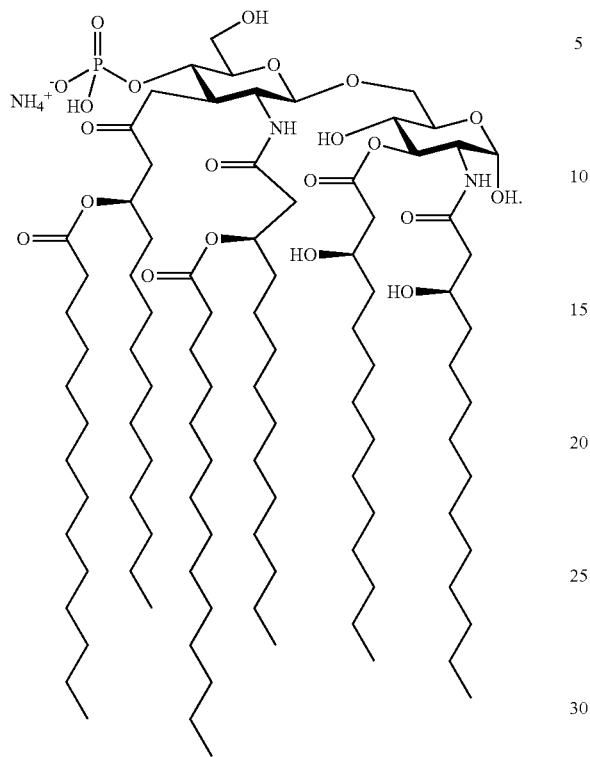
* * * * *

```
                        SEQUENCE LISTING

<160> NUMBER OF SEQ ID NOS: 2

<210> SEQ ID NO 1
<211> LENGTH: 279
<212> TYPE: PRT
<213> ORGANISM: Escherichia coli

<400> SEQUENCE: 1

Phe Ala Cys Lys Thr Ala Asn Gly Thr Ala Ile Pro Ile Gly Gly Gly
1               5                   10                  15

Ser Ala Asn Val Tyr Val Asn Leu Ala Pro Val Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Asn Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Val Pro Thr Gly Gly
145                 150                 155                 160

Cys Asp Val Ser Ala Arg Asp Val Thr Val Thr Leu Pro Asp Tyr Arg
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr His Ala Asp Ala Gly Asn Ser Ile
        195                 200                 205

Phe Thr Asn Thr Ala Ser Phe Ser Pro Ala Gln Gly Val Gly Val Gln
    210                 215                 220

Leu Thr Arg Asn Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
            260                 265                 270

Gly Val Thr Phe Val Tyr Gln
        275

<210> SEQ ID NO 2
<211> LENGTH: 205
<212> TYPE: PRT
<213> ORGANISM: Escherichia coli

<400> SEQUENCE: 2

Gly Val Ala Leu Gly Ala Thr Arg Val Ile Tyr Pro Ala Gly Gln Lys
```

```
1               5                   10                  15
Gln Val Gln Leu Ala Val Thr Asn Asn Asp Glu Asn Ser Thr Tyr Leu
            20                  25                  30

Ile Gln Ser Trp Val Glu Asn Ala Asp Gly Val Lys Asp Gly Arg Phe
            35                  40                  45

Ile Val Thr Pro Pro Leu Phe Ala Met Lys Gly Lys Lys Glu Asn Thr
        50                  55                  60

Leu Arg Ile Leu Asp Ala Thr Asn Asn Gln Leu Pro Gln Asp Arg Glu
65                  70                  75                  80

Ser Leu Phe Trp Met Asn Val Lys Ala Ile Pro Ser Met Asp Lys Ser
                85                  90                  95

Lys Leu Thr Glu Asn Thr Leu Gln Leu Ala Ile Ile Ser Arg Ile Lys
            100                 105                 110

Leu Tyr Tyr Arg Pro Ala Lys Leu Ala Leu Pro Pro Asp Gln Ala Ala
            115                 120                 125

Glu Lys Leu Arg Phe Arg Arg Ser Ala Asn Ser Leu Thr Leu Ile Asn
            130                 135                 140

Pro Thr Pro Tyr Tyr Leu Thr Val Thr Glu Leu Asn Ala Gly Thr Arg
145                 150                 155                 160

Val Leu Glu Asn Ala Leu Val Pro Pro Met Gly Glu Ser Ala Val Lys
                165                 170                 175

Leu Pro Ser Asp Ala Gly Ser Asn Ile Thr Tyr Arg Thr Ile Asn Asp
            180                 185                 190

Tyr Gly Ala Leu Thr Pro Lys Met Thr Gly Val Met Glu
            195                 200                 205
```